United States Patent
Sun et al.

(10) Patent No.: US 11,710,244 B2
(45) Date of Patent: Jul. 25, 2023

(54) SYSTEMS AND METHODS FOR MACHINE LEARNING BASED PHYSIOLOGICAL MOTION MEASUREMENT

(71) Applicant: SHANGHAI UNITED IMAGING INTELLIGENCE CO., LTD., Shanghai (CN)

(72) Inventors: Shanhui Sun, Cambridge, MA (US);
Zhang Chen, Cambridge, MA (US);
Terrence Chen, Cambridge, MA (US);
Ziyan Wu, Cambridge, MA (US)

(73) Assignee: SHANGHAI UNITED IMAGING INTELLIGENCE CO., LTD., Shanghai (CN)

( * ) Notice: Subject to any disclaimer, the term of this patent is extended or adjusted under 35 U.S.C. 154(b) by 95 days.

(21) Appl. No.: 16/673,817

(22) Filed: Nov. 4, 2019

(65) Prior Publication Data

US 2021/0133984 A1 May 6, 2021

(51) Int. Cl.
*G06N 3/08* (2023.01)
*G06T 7/246* (2017.01)
(Continued)

(52) U.S. Cl.
CPC ............ *G06T 7/248* (2017.01); *A61B 5/1076* (2013.01); *A61B 5/1107* (2013.01);
(Continued)

(58) Field of Classification Search
CPC . G06T 2207/20084; G06T 2207/20081; G06T 7/0012; G06T 7/0014;
(Continued)

(56) References Cited

U.S. PATENT DOCUMENTS

| 8,073,523 B2 | 12/2011 | Moghaddam et al. |
| 2003/0083578 A1* | 5/2003 | Abe ............... A61B 8/485 |
| | | 600/447 |

(Continued)

FOREIGN PATENT DOCUMENTS

| CN | 107730567 A | 2/2018 |
| CN | 109389587 A | 2/2019 |

(Continued)

OTHER PUBLICATIONS

Machine translation via Search of FR 2977696 A1, Apr. 21, 2022, 14 pages. (Year: 2022).*

(Continued)

*Primary Examiner* — Matthew C Bella
*Assistant Examiner* — Dennis Rosario
(74) *Attorney, Agent, or Firm* — Metis IP LLC

(57) ABSTRACT

A system for physiological motion measurement is provided. The system may acquire a reference image corresponding to a reference motion phase of an ROI and a target image of the ROI corresponding to a target motion phase, wherein the reference motion phase may be different from the target motion phase. The system may identify one or more feature points relating to the ROI from the reference image, and determine a motion field of the feature points from the reference motion phase to the target motion phase using a motion prediction model. An input of the motion prediction model may include at least the reference image and the target image. The system may further determine a physiological condition of the ROI based on the motion field.

20 Claims, 12 Drawing Sheets

(51) Int. Cl.

| | |
|---|---|
| *A61B 5/11* | (2006.01) |
| *A61B 5/107* | (2006.01) |
| *G06T 7/20* | (2017.01) |
| *G06T 7/62* | (2017.01) |
| *G06T 7/215* | (2017.01) |
| *G06T 7/00* | (2017.01) |
| *G06T 11/00* | (2006.01) |
| *G06F 18/2132* | (2023.01) |
| *G06F 18/214* | (2023.01) |
| *G06F 18/21* | (2023.01) |
| *G06V 10/25* | (2022.01) |
| *G06V 10/764* | (2022.01) |
| *G06V 10/774* | (2022.01) |
| *A61B 90/00* | (2016.01) |

(52) U.S. Cl.
CPC ........ *A61B 5/1128* (2013.01); *G06F 18/2132* (2023.01); *G06F 18/2155* (2023.01); *G06F 18/2178* (2023.01); *G06N 3/08* (2013.01); *G06T 7/0016* (2013.01); *G06T 7/20* (2013.01); *G06T 7/215* (2017.01); *G06T 7/251* (2017.01); *G06T 7/62* (2017.01); *G06T 11/005* (2013.01); *G06V 10/25* (2022.01); *G06V 10/764* (2022.01); *G06V 10/7753* (2022.01); *A61B 2090/061* (2016.02); *G06T 2207/10088* (2013.01); *G06T 2207/20081* (2013.01); *G06T 2207/30048* (2013.01); *G06T 2207/30061* (2013.01)

(58) Field of Classification Search
CPC . G06T 2207/30004; G06T 2207/30048; G06T 7/20; G06T 7/0016; G06T 7/251; G06T 2207/10088; G06T 2207/10081; G06T 2207/10016; G06T 2207/30096; G06T 2207/10116; G06T 7/30; G06T 2207/10132; G06T 2207/10072; G06T 2207/10104; G06T 2207/30068; G06T 2210/41; G06T 2207/20104; G06T 2207/30101; G06T 7/38; G06T 2207/10068; G06T 2207/30081; G06T 2207/10121; G06T 2207/30061; G06T 2207/30241; G06T 3/0068; G06T 11/003; G06T 7/32; G06T 7/344; G06T 2207/10096; G06T 11/008; G06T 2207/10064; G06T 2207/10076; G06T 2207/30056; G06T 2207/30028; G06T 2207/30064; G06T 7/62; G06T 2207/10101; G06T 2207/30041; G06T 7/149; G06T 7/215; G06T 7/579; G06T 2207/10136; G06T 2207/30084; G06T 2211/424; G06T 7/223; G06T 2207/30044; G06T 2207/30104; G06N 3/084; G06N 3/0454; G06N 3/08; G06N 20/00; G06N 3/088; G06N 3/094; G06N 3/02; A61B 5/7264; A61B 5/0044; A61B 5/7275; A61B 8/485; A61B 2576/023; A61B 6/5217; A61B 6/5264; A61B 6/484; A61B 6/485; A61B 6/486; A61B 6/487; A61B 8/5223; A61B 6/032; A61B 6/502; A61B 6/505; A61B 6/025; A61B 8/0825; A61B 8/483; A61B 5/107; A61B 5/1076; A61B 8/469; A61B 2090/376; A61B 2090/374; A61B 2090/3762; A61B 2090/378; A61B 5/341; A61B 5/7271; A61B 5/7296; A61B 6/504; A61B 2034/107; A61B 5/0037; A61B 5/004; A61B 5/11; A61B 5/1107; A61B 8/0883; A61B 8/08; A61B 6/03; A61B 2017/00106; A61B 2576/02; A61B 5/103; A61B 5/1128; A61B 2090/061; A61B 2090/3735; A61B 3/113; A61B 6/469; A61B 6/503; A61B 6/5288; A61B 5/0004; A61B 5/72; A61B 5/4082; A61B 5/4094; A61B 5/721; A61B 8/14; A61B 8/13; A61B 8/15; G06V 10/82; G06V 10/764; G06V 2201/03; G06V 10/454; G06V 10/70; G06V 10/25; G06V 40/20; G06V 10/7753; G06V 40/23; G06V 40/18; G06V 30/18057; G06V 2201/12; G16H 50/20; G16H 30/40; G16H 30/20; G16H 50/30; G16H 50/50

See application file for complete search history.

(56) References Cited

U.S. PATENT DOCUMENTS

| | | | |
|---|---|---|---|
| 2011/0243401 A1* | 10/2011 | Zabair | G06T 7/0012 |
| | | | 382/128 |
| 2014/0270447 A1 | 9/2014 | Fei et al. | |
| 2017/0337682 A1* | 11/2017 | Liao | G06T 7/30 |
| 2018/0116521 A1 | 5/2018 | Kar et al. | |
| 2019/0057505 A1 | 2/2019 | Pheiffer et al. | |
| 2020/0090345 A1* | 3/2020 | Krebs | A61B 5/1116 |
| 2021/0350179 A1* | 11/2021 | Bello | G06F 18/2148 |

FOREIGN PATENT DOCUMENTS

| | | | | |
|---|---|---|---|---|
| CN | 110148150 A | | 8/2019 | |
| FR | 2977696 A1 * | | 1/2013 | ............... G06T 7/37 |
| WO | WO-2010079690 A1 * | | 7/2010 | ............ A61B 5/0059 |

OTHER PUBLICATIONS

Search machine tranlation Video Image Display Device and Program of WO 2010/079690 A1 to OSAMU, retrieved Sep. 24, 2022, 15 pages. (Year: 2022).*

Bello et al., Deep-learning cardiac motion analysis for human survival prediction; Feb. 11, 2019 [retrieved Mar. 2, 2023], Nature Machine Intelligence, vol. 1, Issue: 2, 16 pages. Retrieved: (Year: 2019).*

[item U continued] https://research.birmingham.ac.uk/en/publications/deep-learning-cardiac-motion-analysis-for-human-survival-predicti (Year: 2019).*

Z. Rahman et al., Feature Tracking Cardiac Magnetic Resonance Imaging: A Review of a Novel Non-invasive Cardiac imaging Technique, World Journal of Cardiol, 9(4): 312-319, 2017.

M. Jaderberg et al., Spatial Transformer Networks, NIPS 2015, 14 pages.

I. Goodfellow et al., Generative Adversarial Nets, NIPS 2014, 9 pages.

P. Isola et al., Image-to-image Translation with Conditional Adversarial Networks, IEEE Conference on Computer Vision and Pattern Recognition, 2017, 10 pages.

Zhu, Jin et al., A Model Based on Local Displacement Fitting with BPNN for Calculating Myocardial Deformation, Journal of Computer Research and Development, 42(12): 2143-2148, 2005.

Li, Jiahao el al., Unmanned Vehicle Night Infrared Video Colorization Based on Dual-Channel Cycle-Consistent Adversarial Networks, Laser & Optoelectronics Progress, 2018, 7 pages.

Joyita Dutta et al., Accuracy of Respiratory Motion Compensated image Reconstruction Using 4DPET-Derived Deformation Fields, IEEE, 2014, 4 pages.

* cited by examiner

500

| 501 | Acquiring a plurality of images indicative of a physiological motion of an ROI, the images including at least a reference image of the ROI corresponding to a reference motion phase and a target image of the ROI corresponding to a target motion phase |

| 502 | Identifying one or more feature points relating to the ROI from the reference image |

| 503 | Determining a motion field of the one or more feature points from the reference motion phase to the target motion phase using a motion prediction model |

| 504 | Determining, based on the motion field, a physiological condition of the ROI |

FIG. 5

SYSTEMS AND METHODS FOR MACHINE LEARNING BASED PHYSIOLOGICAL MOTION MEASUREMENT

TECHNICAL FIELD

The present disclosure generally relates to physiological motion measurement, and more particularly, methods and systems for measuring a physiological motion of a region of interest (ROI) based on a machine learning technique.

BACKGROUND

Medical imaging is widely used in disease diagnosis and/or treatment. A subject, such as a patient, may be scanned by a medical imaging device to acquire image data of the subject for analysis. In some occasions, an ROI of the subject may undergo a physiological motion (e.g., a cardiac motion, a respiratory motion, etc.) during the scan and a plurality of images of the ROI corresponding to a plurality of motion phases may be generated. The images of the ROI corresponding to different motion phases may be used to evaluate a physiological condition of the ROI. For example, by performing a magnetic resonance (MR) scan on the heart of a patient, a plurality of cardiac MR imaging (CMRI) cine images may be acquired for assessing the myocardial function of the patient. Thus, it is desirable to provide effective systems and methods for physiological motion measurement, thereby improving the accuracy of disease diagnosis and/or treatment.

SUMMARY

According to one aspect of the present disclosure, a system for physiological motion measurement is provided. The system may include at least one storage device including a set of instructions for physiological motion measurement, and at least one processor configured to communicate with the at least one storage device. When executing the instructions, the at least one processor may be configured to direct the system to perform the following operations. The at least one processor may be configured to direct the system to acquiring a reference image of an ROI corresponding to a reference motion phase of the ROI and a target image of the ROI corresponding to a target motion phase of the ROI, the target motion phase being different from the reference motion phase. The at least one processor may be also configured to direct the system to identify one or more feature points relating to the ROI from the reference image. The at least one processor may be further configured to direct the system to determine a motion field of the one or more feature points from the reference motion phase to the target motion phase using a motion prediction model, wherein an input of the motion prediction model includes at least the reference image and the target image. The at least one processor may be further configured to direct the system to determine a physiological condition of the ROI based on the motion field.

In some embodiments, the ROI may include at least one of a heart, a lung, an abdomen, a chest, a stomach, or of a subject.

In some embodiments, the ROI may be a heart, and the one or more feature points relating to the heart in the reference image may include an inner point on an endocardium of the heart and a corresponding outer point on an epicardium of the heart.

In some embodiments, to identify the inner point and the corresponding outer point from the reference image, the at least one processor may be configured to direct the system to segment the endocardium and the epicardium from the reference image, and identify the inner point and the corresponding outer point from the reference image based on the positions of the endocardium and the epicardium.

In some embodiments, the motion field may include one or more motion vectors corresponding to the one or more features points. To determine a physiological condition of the heart, the at least one processor may be configured to direct the system to determine a first distance between the inner point and the corresponding outer point in the reference motion phase based on the reference image. The at least one processor may also be configured to direct the system to determine a second distance between the inner point and the corresponding outer point in the target motion phase based on the motion vector of the inner point and the motion vector of the outer point. The at least one processor may further be configured to direct the system to determine a strain value relating to the heart based on the first distance and the second distance.

In some embodiments, the motion prediction model may be trained according to a supervised training process. The supervised training process may include obtaining at least one annotated training sample. Each of the at least one annotated training sample may include a first annotated image of a sample ROI corresponding to a first motion phase, a second annotated image of the sample ROI corresponding to a second motion phase, and a sample motion field between the first annotated image and the second annotated image. The first annotated image may be annotated with one or more first sample feature points relating to the sample ROI, and the second annotated image may be annotated with one or more second sample feature points corresponding to the first sample feature points. The supervised training process may also include generating the motion prediction model by training a preliminary model using the at least one annotated training sample according to a supervised learning technique.

In some embodiments, the motion prediction model may be trained according to an unsupervised training process. The unsupervised training process may include obtaining at least one training sample. Each of the at least one training sample may include a first image of a sample ROI in a first motion phase and a second image of the sample ROI in a second motion phase. The unsupervised training process may further include generating the motion prediction model by training a preliminary model using the at least one training sample according to an unsupervised learning technique.

In some embodiments, the preliminary model may be a generative adversarial network (GAN) model.

According to one aspect of the present disclosure, a system for generating a motion prediction model is provided. The system may include at least one storage device storing a set of instructions for generating a motion prediction model, and at least one processor configured to communicate with the at least one storage device. When executing the instructions, the at least one processor may be configured to direct the system to perform the following operations. The at least one processor may be configured to direct the system to obtain at least one training sample. Each training sample may include a first image and a second image indicative of a physiological motion of a sample ROI. The first image may correspond to a first motion phase of the sample ROI, and the second image may correspond to a second motion phase of the sample ROI. The at least one processor may also be configured to direct the system to generate the motion prediction model by training a preliminary model using the at least one training sample according to an unsupervised learning technique.

In some embodiments, to generate the motion prediction model by training a preliminary model, the at least one processor may be configured to direct the system to train the preliminary model by minimizing a loss function, and designate at least a portion of the trained preliminary model as the motion prediction model. The loss function may relate to a difference between the second image of the training sample and a predicted second image. The predicted second image may be generated based on the first image and the second image of the training sample and the preliminary model.

In some embodiments, the training the preliminary model by minimizing a loss function may include an iterative operation including one or more iterations. For each of the at least one training sample, at least one iteration of the iterative operation may include generating a first motion field from the first image to the second image using an updated preliminary model determined in a previous iteration, and generating a predicted second image by warping the first image of the training sample according to the first motion field. For each of the at least one training sample, the at least one iteration of the iterative operation may also include determining a first difference between the predicted second image and the second image of the training sample, and determining a value of the loss function based at least in part on the first difference corresponding to each of the at least one training sample. For each of the at least one training sample, the at least one iteration of the iterative operation may further include updating the updated preliminary model to be used in a next iteration.

In some embodiments, for each of the at least one training sample, the at least one processor may be further configured to direct the system to generate a second motion field from the second image to the first image using the preliminary model, and determine an opposite motion field of the second motion field. For each of the at least one training sample, the at least one processor may further be configured to direct the system to determine a second difference between the opposite motion field and the first motion field of the training sample. The value of the loss function may be determined further based on the second difference corresponding to each training sample.

In some embodiments, for each of the at least one training sample, the at least one processor may be configured to direct the system to generate a predicted first image by warping the second image of the training sample according to the first image of the training sample using the preliminary model. For each of the at least one training sample, the at least one processor may also be configured to direct the system to generate a third image by warping the predicted first image according to the second image using the preliminary model, and generate a fourth image by warping the predicted second image according to the first image using the preliminary model. For each of the at least one training sample, the at least one processor may further be configured to direct the system to determine a third difference between the third image and the second image and a fourth difference between the fourth image and the first image. The value of the loss function may be determined further based on the third difference and the fourth difference corresponding to each training sample.

In some embodiments, the preliminary model may include a generator. For each of the at least one training sample, the generator may be configured to predict a first motion field from the first image of the training sample to the second image of the training sample.

In some embodiments, the preliminary model may further include a transformation layer. For each of the at least one training sample, the transformation layer may be configured to warp the first image of the training sample according to the corresponding first motion field to generate the corresponding predicted second image.

In some embodiments, the preliminary model may further include a discriminator. For each of the at least one training sample, the discriminator may be configured to generate a discrimination result between the second image of the training sample and the corresponding predicted second image. The value of the loss function may be determined further based on the discrimination result of each training sample.

In some embodiments, the preliminary model may further include a second generator. For each training sample, the second generator may be configured to predict a second motion field from the second image of the training sample to the first image of the training sample based on the first image and the second image of the training sample.

In some embodiments, the training the preliminary model may include training the generator. The designating at least one a portion of the trained preliminary model as the motion prediction model may include designating the trained generator as the motion prediction model.

In some embodiments, the at least one processor may be configured to direct the system to obtain a first annotated image of the sample ROI corresponding a third motion phase and an unannotated image of the sample ROI corresponding a fourth motion phase. The first annotated image may include an annotation of a first feature point relating to the ROI. The at least one processor may also be configured to direct the system to determine a motion field of the first feature point from the third motion phase to the fourth motion phase by applying the motion prediction model to the first annotated image and the unannotated image. The at least one processor may further be configured to direct the system to generate a second annotated image of the sample ROI corresponding the fourth motion phase based on the annotation of the first feature point and the motion field. The second annotated image may include an annotation of a second feature point corresponding to the first feature point.

According to another aspect of the present disclosure, a non-transitory computer-readable storage medium including a set of instructions for physiological motion measurement is provided. When executed by at least one processor, the set of instructions direct the at least one processor to effectuate a method. The method may include acquiring a reference image of an ROI corresponding to a reference motion phase of the ROI and a target image of the ROI corresponding to a target motion phase of the ROI, wherein the target motion phase may be different from the reference motion phase. The method may also include determining a motion field of the one or more feature points from the reference motion phase to the target motion phase using a motion prediction model, wherein an input of the motion prediction model includes at least the reference image and the target image. The method may further include determining a physiological condition of the ROI based on the motion field.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 5 is a flowchart illustrating an exemplary process for determining a physiological condition of an ROI according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
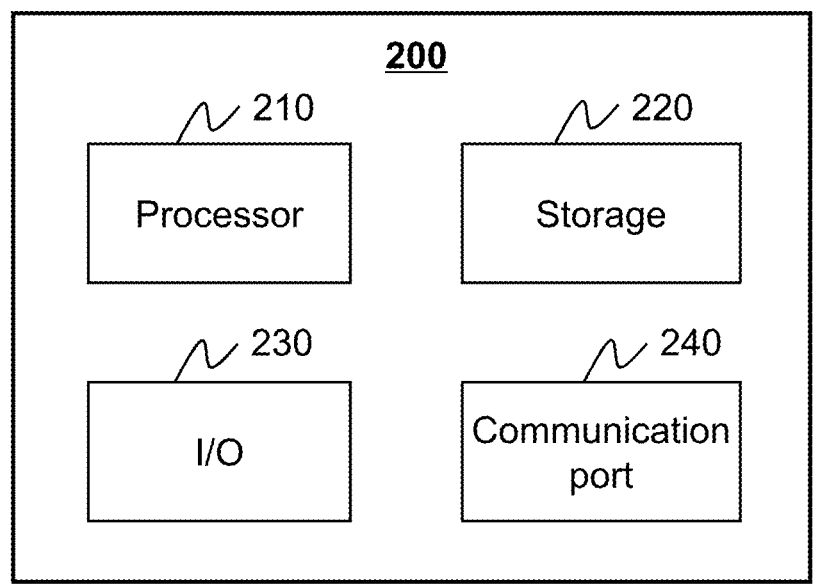
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive biomedical imaging, such as for disease diagnostic or research purposes. In some embodiments, the systems may include a single modality imaging system and/or a multi-modality imaging system. The single modality imaging system may include, for example, an ultrasound imaging system, an X-ray imaging system, an computed tomography (CT) system, a magnetic resonance imaging (MRI) system, an ultrasonography system, a positron emission tomography (PET) system, an optical coherence tomography (OCT) imaging system, an ultrasound (US) imaging system, an intravascular ultrasound (IVUS) imaging system, a near infrared spectroscopy (NIRS) imaging system, a far infrared (FIR) imaging system, or the like, or any combination thereof. The multi-modality imaging system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a C-arm system, a digital subtraction angiography-magnetic resonance imaging (DSA-MRI) system, etc. It should be noted that the imaging system described below is merely provided for illustration purposes, and not intended to limit the scope of the present disclosure.

The term "imaging modality" or "modality" as used herein broadly refers to an imaging method or technology that gathers, generates, processes, and/or analyzes imaging information of a subject. The subject may include a biological subject and/or a non-biological subject. The biological subject may be a human being, an animal, a plant, or a portion thereof (e.g., a cell, a tissue, an organ, etc.). In some embodiments, the subject may be a man-made composition of organic and/or inorganic matters that are with or without life.

An aspect of the present disclosure relates to systems and methods for physiological motion measurement. The systems and methods may acquire a reference image corresponding to a reference motion phase of an ROI (e.g., the heart or a lung of a patient) and a target image corresponding to a target motion phase of the ROI, wherein the target motion phase being different from the reference motion phase. The systems and methods may identify one or more feature points relating to the ROI from the reference image. The systems and methods may also determine a motion field of the feature point(s) from the reference motion phase to the target motion phase using a motion prediction model, wherein an input of the motion prediction model may include at least the reference image and the target image. The systems and methods may further determine a physiological condition of the ROI based on the motion field.

According to some embodiments of the present disclosure, the motion field of the feature point(s) from the reference motion phase to the target motion phase may be determined using a motion prediction model. The motion prediction model may be a neural network model that is configured to receive two images corresponding to different motion phases of the ROI as an input and output a motion field between the two images. In some embodiments of the present disclosure, the physiological motion measurement of the ROI does not rely on a prior defined shape model of the ROI. Instead, a motion prediction model, which learns an optimal mechanism for determining a motion field between two images from training data, may be used for physiological motion measurement. This may improve the accuracy and reliability of the measurement result. In addition, in some embodiments, the motion prediction model may be trained using one or more training samples according to an unsupervised learning technique (or referred to as an unsupervised training process or technique). Also, this may obviate the need for annotating the training sample(s), which may improve the efficiency of training the motion prediction model and/or automate the training process.

Figure 1:
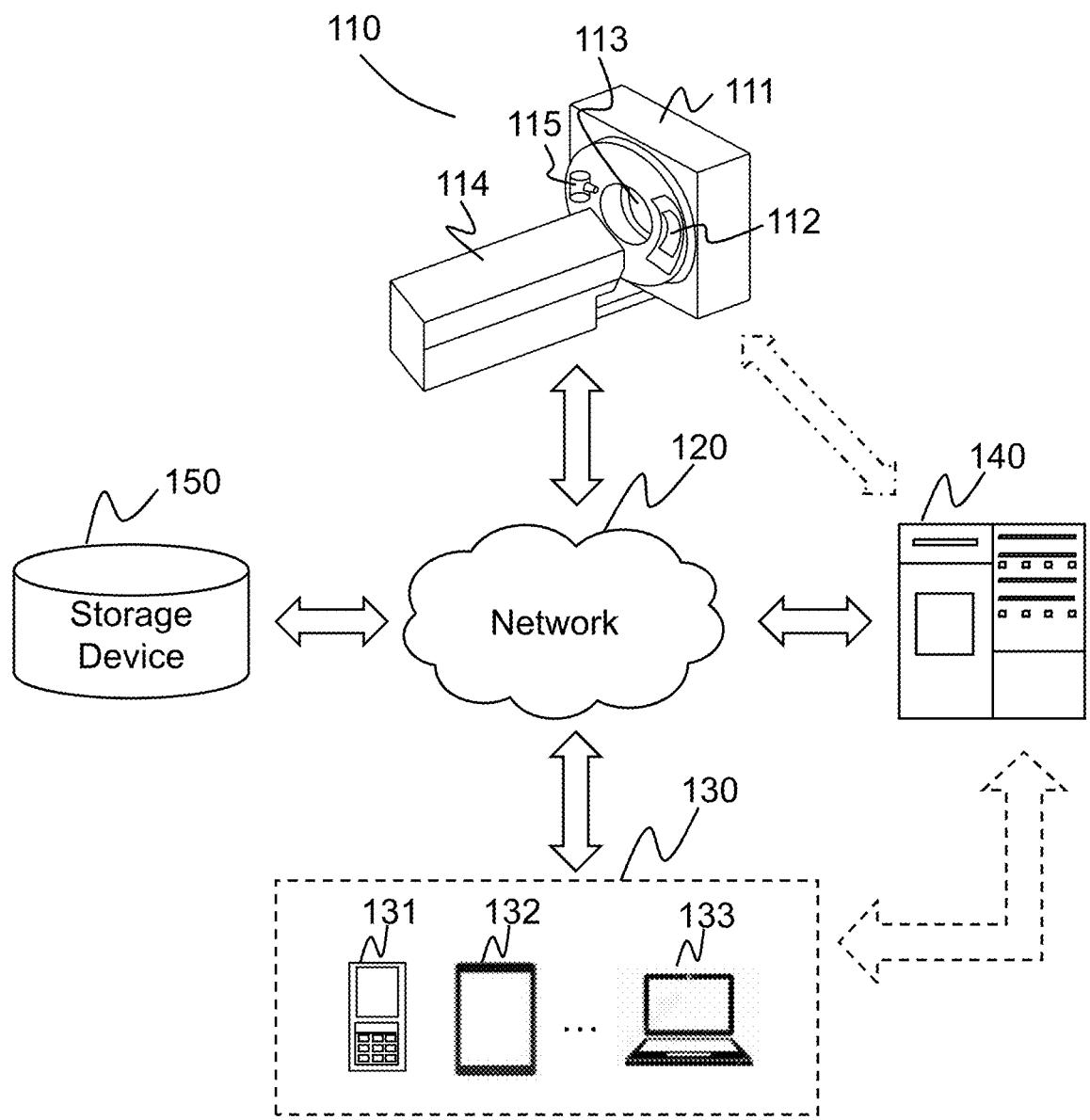
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. As shown, the imaging system 100 may include an imaging device 110, a network 120, one or more terminals 130, a processing device 140, and a storage device 150. In some embodiments, the imaging device 110, the terminal(s) 130, the processing device 140, and/or the storage device 150 may be connected to and/or communicate with each other via a wireless connection (e.g., the network 120), a wired connection, or a combination thereof. The connection between the components of the imaging system 100 may be variable. Merely by way of example, the imaging device 110 may be connected to the processing device 140 through the network 120, as illustrated in FIG. 1. As another example, the imaging device 110 may be connected to the processing device 140 directly or through the network 120. As a further example, the storage device 150 may be connected to the processing device 140 through the network 120 or directly.

The imaging device 110 may generate or provide image data related to a subject via scanning the subject. In some embodiments, the subject may include a biological subject and/or a non-biological subject. For example, the subject may include a specific portion of a body, such as a head, a thorax, an abdomen, or the like, or a combination thereof. In some embodiments, the imaging device 110 may include a single-modality scanner (e.g., an MRI device, a CT scanner) and/or multi-modality scanner (e.g., a PET-CT scanner) as described elsewhere in this disclosure. In some embodiments, the image data relating to the subject may include projection data, one or more images of the subject, etc. The projection data may include raw data generated by the imaging device 110 by scanning the subject and/or data generated by a forward projection on an image of the subject.

In some embodiments, the imaging device 110 may include a gantry 111, a detector 112, a detecting region 113, a scanning table 114, and a radioactive scanning source 115. The gantry 111 may support the detector 112 and the radioactive scanning source 115. The object may be placed on the scanning table 114 to be scanned. The radioactive scanning source 115 may emit radioactive rays to the object. The radiation may include a particle ray, a photon ray, or the like, or a combination thereof. In some embodiments, the radiation may include a plurality of radiation particles (e.g., neutrons, protons, electron, p-mesons, heavy ions), a plurality of radiation photons (e.g., X-ray, a g-ray, ultraviolet, laser), or the like, or a combination thereof. The detector 112 may detect radiations and/or radiation events (e.g., gamma photons) emitted from the detecting region 113. In some embodiments, the detector 112 may include a plurality of detector units. The detector units may include a scintillation detector (e.g., a cesium iodide detector) or a gas detector. The detector unit may be a single-row detector or a multi-rows detector.

The network 120 may include any suitable network that can facilitate the exchange of information and/or data for the imaging system 100. In some embodiments, one or more components of the imaging system 100 (e.g., the imaging device 110, the processing device 140, the storage device 150, the terminal(s) 130) may communicate information and/or data with one or more other components of the imaging system 100 via the network 120. For example, the processing device 140 may obtain image data from the imaging device 110 via the network 120. As another example, the processing device 140 may obtain user instruction(s) from the terminal(s) 130 via the network 120.

The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may be connected to and/or communicate with the imaging device 110, the processing device 140, and/or the storage device 150. For example, the terminal(s) 130 may display a physiological condition of an ROI of the subject. In some embodiments, the terminal(s) 130 may include a mobile device 131, a tablet computer 132, a laptop computer 133, or the like, or any combination thereof. For example, the mobile device 131 may include a mobile phone, a personal digital assistant (PDA), a gaming device, a navigation device, a point of sale (POS) device, a laptop, a tablet computer, a desktop, or the like, or any combination thereof. In some embodiments, the terminal(s) 130 may include an input device, an output device, etc. In some embodiments, the terminal(s) 130 may be part of the processing device 140.

The processing device 140 may process data and/or information obtained from the imaging device 110, the storage device 150, the terminal(s) 130, or other components of the imaging system 100. In some embodiments, the processing device 140 may be a single server or a server group. The server group may be centralized or distributed. For example, the processing device 140 may generate a motion prediction model by training a preliminary model using one or more training samples. As another example, the processing device 140 may apply the motion prediction model in physiological motion measurement. In some embodiments, the motion prediction model may be generated by a processing device, while the application of the motion prediction model may be performed on a different processing device. In some embodiments, the motion prediction model may be generated by a processing device of a system different than the imaging system 100 or a server different than the processing device 140 on which the application of the motion prediction model is performed. For instance, the motion prediction model may be generated by a first system of a vendor who provides and/or maintains such a motion prediction model, while the physiological motion measurement based on the provided motion prediction model may be performed on a second system of a client of the vendor. In some embodiments, the application of the motion prediction model may be performed online in response to a request for physiological motion measurement. In some embodiments, the motion prediction model may be determined or generated offline.

In some embodiments, the processing device 140 may be local to or remote from the imaging system 100. For example, the processing device 140 may access information and/or data from the imaging device 110, the storage device 150, and/or the terminal(s) 130 via the network 120. As another example, the processing device 140 may be directly connected to the imaging device 110, the terminal(s) 130, and/or the storage device 150 to access information and/or data. In some embodiments, the processing device 140 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 140 may be implemented by a computing device 200 having one or more components as described in connection with FIG. 2.

In some embodiments, the processing device 140 may include one or more processors (e.g., single-core processor(s) or multi-core processor(s)). Merely by way of example, the processing device 140 may include a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

The storage device 150 may store data, instructions, and/or any other information. In some embodiments, the storage device 150 may store data obtained from the processing device 140, the terminal(s) 130, and/or the imaging device 110. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components of the imaging system 100 (e.g., the processing device 140, the terminal(s) 130). One or more components of the imaging system 100 may access the data or instructions stored in the storage device 150 via the network 120. In some embodiments, the storage device 150 may be part of the processing device 140.

It should be noted that the above description of the imaging system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the imaging system 100 may include one or more additional components. Additionally or alternatively, one or more components of the imaging system 100 described above may be omitted. As another example, two or more components of the imaging system 100 may be integrated into a single component.

FIG. 2 is a schematic diagram illustrating exemplary hardware and/or software components of a computing device 200 according to some embodiments of the present disclosure. The computing device 200 may be used to implement any component of the imaging system 100 as described herein. For example, the processing device 140 and/or the terminal 130 may be implemented on the computing device 200, respectively, via its hardware, software program, firmware, or a combination thereof. Although only one such computing device is shown, for convenience, the computer functions relating to the imaging system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the imaging device 110, the terminal(s) 130, the storage device 150, and/or any other component of the imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging device 110, the terminal(s) 130, the storage device 150, and/or any other component of the imaging system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure. For example, the storage 220 may store a program for the processing device 140 to execute to generate a motion prediction model.

The I/O 230 may input and/or output signals, data, information, etc. In some embodiments, the I/O 230 may enable a user interaction with the processing device 140. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 140) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the processing device 140 and the imaging device 110, the terminal(s) 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
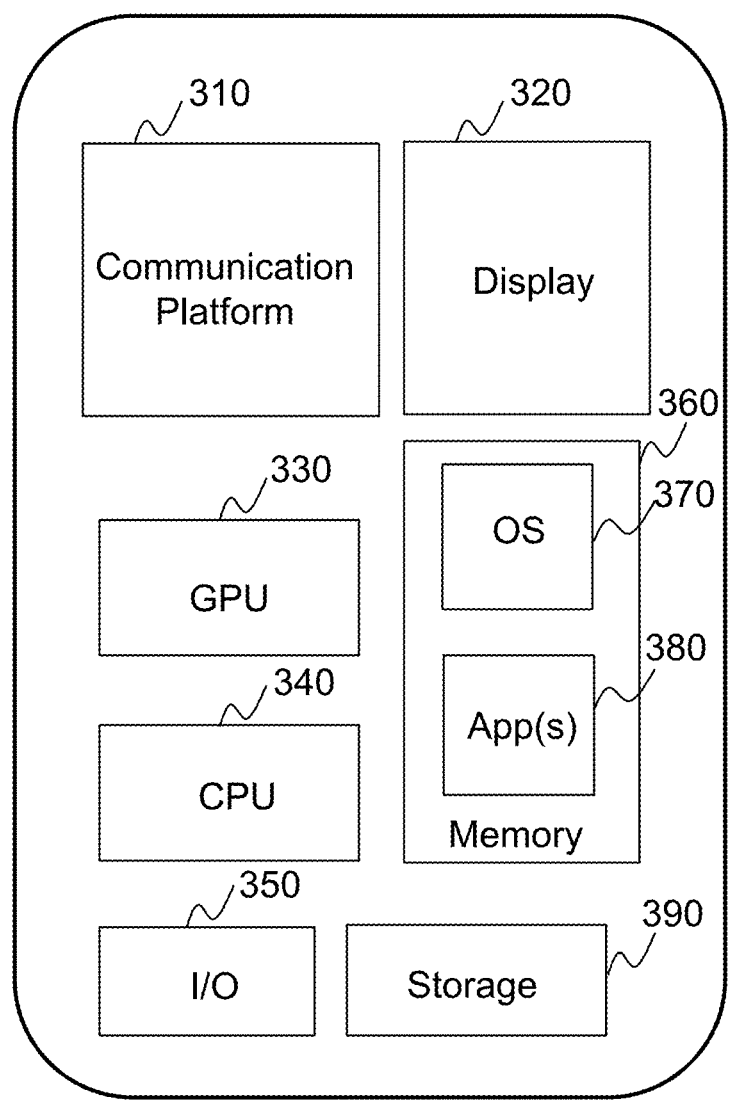
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device 300 according to some embodiments of the present disclosure. In some embodiments, one or more components (e.g., a terminal 130 and/or the processing device 140) of the imaging system 100 may be implemented on the mobile device 300.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4A:
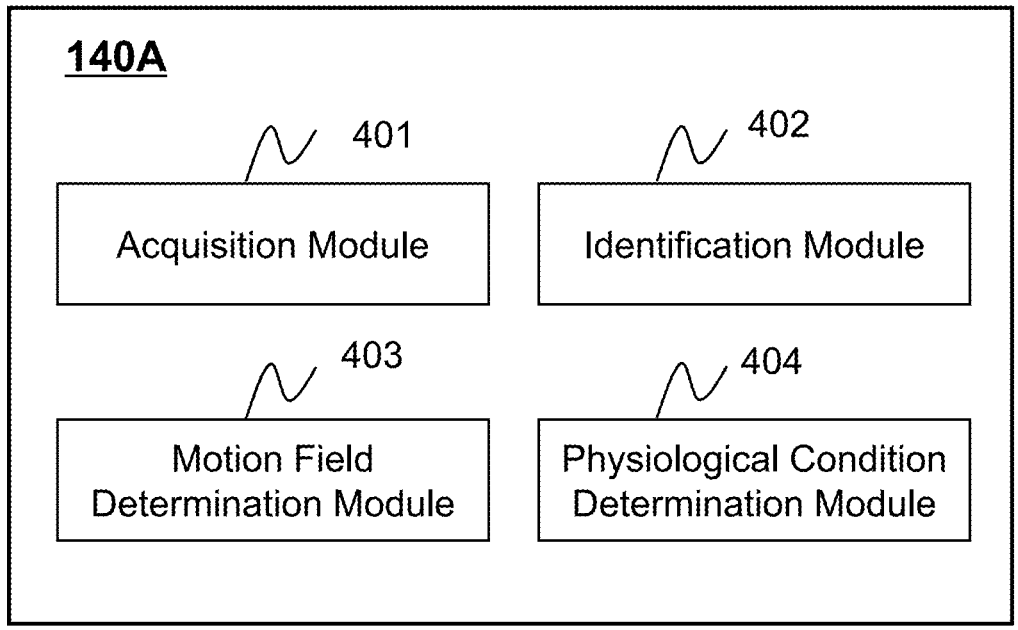
FIGS. 4A and 4B are block diagrams illustrating exemplary processing devices according to some embodiments of the present disclosure.
Figure 4B:
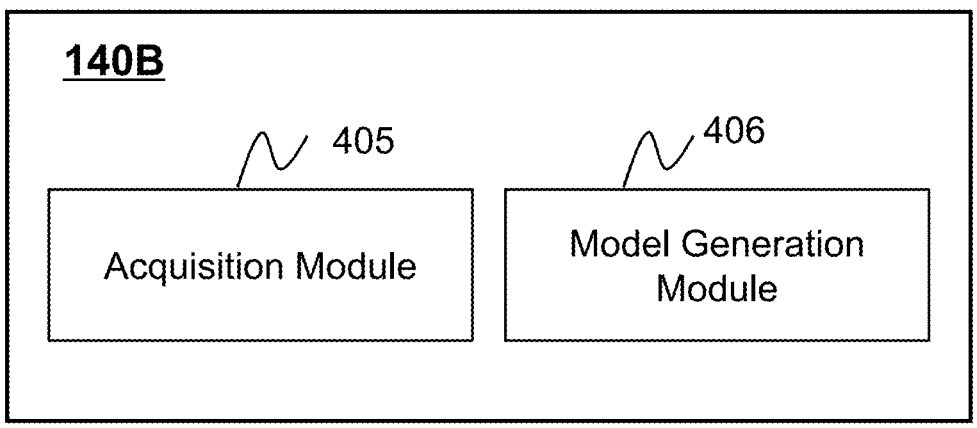

FIGS. 4A and 4B are block diagrams illustrating exemplary processing devices 140A and 140B according to some embodiments of the present disclosure. The processing devices 140A and 140B may be exemplary processing devices 140 as described in connection with FIG. 1. In some embodiments, the processing device 140A may be configured to apply a motion prediction model in physiological condition measurement. The processing device 140B may be configured to obtain one or more training samples and/or generate the motion prediction model using the training samples. In some embodiments, the processing devices 140A and 140B may be respectively implemented on a processing unit (e.g., a processor 210 illustrated in FIG. 2 or a CPU 340 as illustrated in FIG. 3). Merely by way of example, the processing devices 140A may be implemented on a CPU 340 of a terminal device, and the processing device 140B may be implemented on a computing device 200. Alternatively, the processing devices 140A and 140B may be implemented on a same computing device 200 or a same CPU 340. For example, the processing devices 140A and 140B may be implemented on a same computing device 200.

As shown in FIG. 4A, the processing device 140A may include an acquisition module 401, an identification module 402, a motion field determination module 403, and a physiological condition determination module 404.

The acquisition module 401 may be configured to acquire a plurality of images indicative of a physiological motion of an ROI. The images indicative of the physiological motion of the ROI may correspond to a plurality of motion phases of the ROI. For example, the images may correspond to a plurality of cardiac phases and indicative of a cardiac motion of the heart. In some embodiments, the images may include at least a reference image of the ROI corresponding to a reference motion phase and a target image of the ROI corresponding to a target motion phase. The images may be obtained by an image acquisition device via scanning a patient or retrieved from a storage device. More descriptions regarding the acquisition of the images indicative of the physiological motion of the ROI may be found elsewhere in the present disclosure. See, e.g., operation 501 in FIG. 5 and relevant descriptions thereof.

The identification module 402 may be configured to identify one or more feature points relating to the ROI from the reference image. A feature point may refer to a representative point of the ROI which can be used to measure the physiological motion of the ROI. In some embodiments, the feature point(s) may be identified from the reference image according to a user input, or by the processing device 140A automatically or semi-automatically. More descriptions regarding the identification of the feature point(s) may be found elsewhere in the present disclosure. See, e.g., operation 502 in FIG. 5 and relevant descriptions thereof.

The motion field determination module 403 may be configured to determine a motion field of the feature point(s) from the reference motion phase to the target motion phase using a motion prediction model. The motion field of the feature point(s) may include one or more motion vectors, each of which corresponds to one of the feature points. The motion prediction model may receive a pair of images corresponding to two different motion phases of the ROI, and output a motion field between (or with respect to) the pair of images. More descriptions regarding the determination of the motion field of the feature points may be found elsewhere in the present disclosure. See, e.g., operation 503 in FIG. 5 and relevant descriptions thereof.

The physiological condition determination module 404 may be configured to determine a physiological condition of the ROI based on the motion field. The physiological condition of the ROI may indicate a health status of the ROI. In some embodiments, based on the motion field, the physiological condition determination module 404 may determine a value of a biological parameter indicating the physiological condition of the ROI, an analyzing result of the physiological condition of the ROI, or the like, or any combination thereof. More descriptions regarding the determination of the physiological condition of the ROI may be found elsewhere in the present disclosure. See, e.g., operation 504 in FIG. 5 and relevant descriptions thereof.

As shown in FIG. 4B, the processing device 140B may include an acquisition module 405 and a model generation module 406.

The acquisition module 405 may be configured to obtain one or more training samples. Each training sample may include a first image and a second image indicative of a physiological motion of a sample ROI, wherein the first and second images may correspond to a first motion phase and a second motion field of the sample ROI, respectively. More descriptions regarding the acquisition of the training samples may be found elsewhere in the present disclosure. See, e.g., operation 601 in FIG. 6 and relevant descriptions thereof.

The model generation module 406 may be configured to generate the motion prediction model by training a preliminary model using the training samples according to an unsupervised learning technique. In some embodiments, the model generation module 406 may train the preliminary model by minimizing a loss function. At least a portion of the trained preliminary model may be designated as the motion prediction model. More descriptions regarding the generation of the motion prediction model may be found elsewhere in the present disclosure. See, e.g., operation 602 in FIG. 6 and relevant descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 140A and/or the processing device 140B may share two or more of the modules, and any one of the modules may be divided into two or more units. For instance, the processing devices 140A and 140B may share a same acquisition module; that is, the acquisition module 401 and the acquisition module 405 are a same module. In some embodiments, the processing device 140A and/or the processing device 140B may include one or more additional modules, such a storage module (not shown) for storing data. In some embodiments, the processing device 140A and the processing device 140B may be integrated into one processing device 140.

FIG. 5 is a flowchart illustrating an exemplary process for determining a physiological condition of an ROI according to some embodiments of the present disclosure. In some embodiments, process 500 may be executed by the imaging system 100. For example, the process 500 may be implemented as a set of instructions (e.g., an application) stored in a storage device (e.g., the storage device 150, the storage 220, and/or the storage 390). In some embodiments, the processing device 140A (e.g., the processor 210 of the computing device 200, the CPU 340 of the mobile device 300, and/or one or more modules illustrated in FIG. 4A) may execute the set of instructions and may accordingly be directed to perform the process 500.

Figure 8:
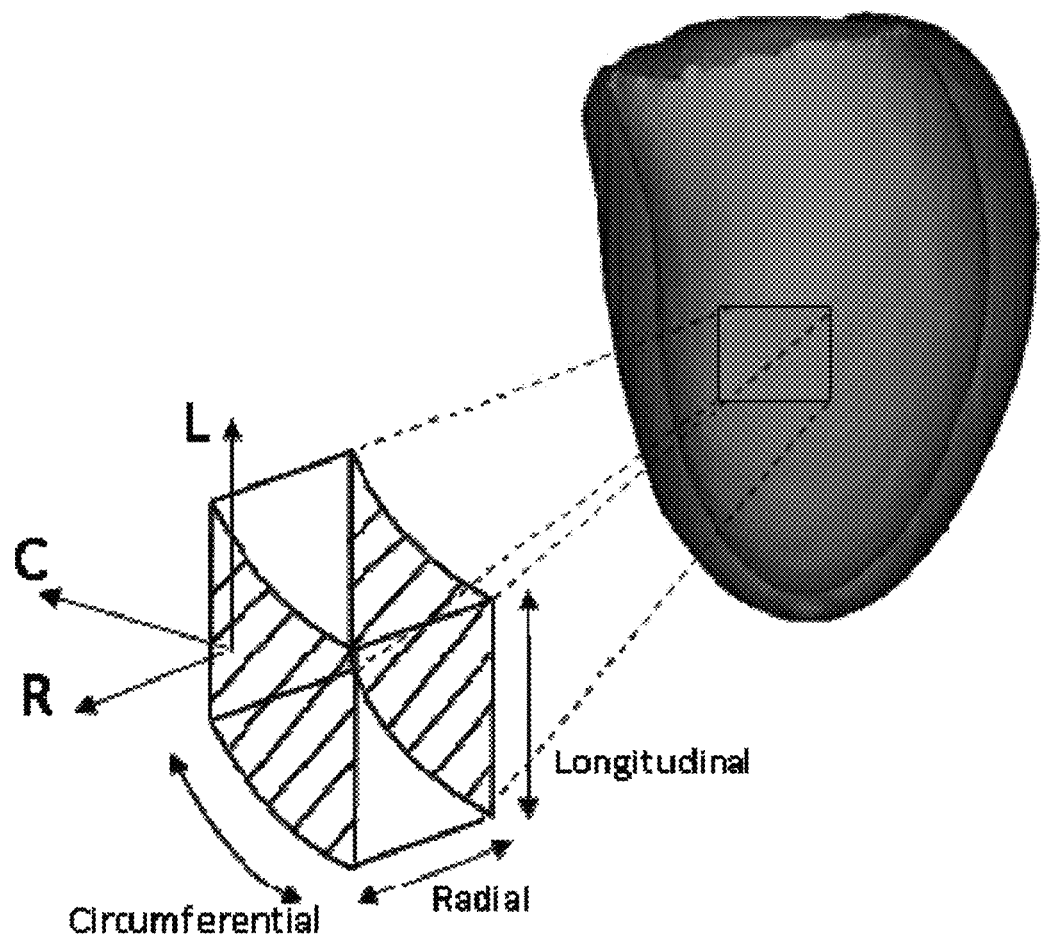
FIG. 8 is a schematic diagram illustrating the cardiac motion of a heart according to some embodiments of the present disclosure.

As used herein, an ROI may include any region of a subject (e.g., a patient or another organism) that undergoes a physiological motion. For illustration purposes, the following descriptions take a patient as an exemplary subject, and not intended to limit the scope of the present disclosure. Exemplary ROIs of a patient may be the heart that undergoes a cardiac motion, a lung that undergoes a respiratory motion, a region filled with blood which forms a blood flow, the stomach that undergoes a gastrointestinal motion, the brain that undergoes a brain motion (e.g., has a brain blood flow), a chest that has a physiological motion caused by the cardiac motion, an abdomen that has a physiological motion caused by the respiratory motion, or the like, or any combination thereof. In some embodiments, the ROI may include the heart of the patient. As illustrated in FIG. 8, the heart may undergo contraction and relaxation motions in a radial direction, a circumferential direction, and a longitudinal direction.

In 501, the processing device 140A (e.g., the acquisition module 401, the interface circuits of the processor 210) may acquire a plurality of images indicative of the physiological motion of the ROI.

The images indicative of the physiological motion of the ROI may correspond to a plurality of motion phases of the ROI. For example, a cardiac cycle may include systole (during which the left and right ventricles contract and eject blood into the aorta and pulmonary artery, respectively) and diastole (during which the ventricles are relaxed). The cardiac cycle may be divided into a plurality of cardiac phases, such as 5 or 10 cardiac phases depending on, for example, the heart rate and/or movement amplitude of the heart. The images may correspond to the plurality of cardiac phases and indicative of the cardiac motion of the heart. As another example, a respiratory cycle may include an inspiratory phase (during which the chest of the subject expands and air flows into the lungs) and an expiratory phase (during which the chest shrinks and the air is pushed out of the lungs). The respiratory cycle may be gated into a plurality of respiratory phases, such as 4 respiratory phases including a mid-inspiratory phase, an end-inspiratory phase, a mid-expiratory phase, and an end-expiratory phase according to, for example, time or the amplitude of the respiratory motion. The images may correspond to the plurality of respiratory phases and indicative of the respiratory motion of the lung.

In some embodiments, the images may include at least a reference image of the ROI corresponding to a reference motion phase and a target image of the ROI corresponding to a target motion phase. The reference motion phase and the target motion phase may be any two different motion phases of the ROI. Merely by way of example, for the cardiac motion, the reference motion phase may be an end of diastole (ED) phase and the target motion phase may an end of systole (ES) phase, or the reference motion phase may be an ES phase and the target motion phase may be an ED phase. As another example, for the respiratory motion, the reference motion phase may be an end-inspiratory phase and the target motion phase may an end-expiratory phase, or the reference motion phase may be an end-expiratory phase and the target motion phase may be an end-inspiratory phase.

In some embodiments, the images may include a 2D image (e.g., a slice image), a 3D image, a 4D image (e.g., a series of 3D images with respect to time), and/or any related image data (e.g., scan data, projection data, etc.). In some embodiments, the images may be reconstructed based on image data acquired using an image acquisition device, such as the imaging device 110 of the system 100 or an external image acquisition device. For example, the images may be acquired by a CT device, an MRI device, an ultrasonography system, an X-ray device, a PET device, or the like, by performing a scan of the patient. In some embodiments, the images may include a plurality of cardiac MRI (CMRI) images acquired by an MRI device by executing an MR scan on the patient. During the MR scan, an electrocardiogram (ECG) signal representing the cardiac motion of the patient may be acquired. A cardiac cycle of the patient may be divided into a plurality of cardiac phases according to the ECG signal, and the image data acquired in the MR scan may be divided into a plurality of image data sets corresponding to the cardiac phases. Then, the CMRI images may be reconstructed based on the image data sets. In some embodiments, the CMRI images may include short-axis image(s) (e.g., images 901 and 902 in FIG. 9A) and/or long-axis image(s) (e.g., images 907 and 908 in FIG. 9B) of the heart. A long-axis image may illustrate a cross-section of the heart along the longitudinal direction as illustrated in FIG. 8. A short-axis image may illustrate a cross-section of the heart that is perpendicular to the longitudinal direction. In some embodiments, the images may be previously generated and stored in a storage device (e.g., the storage device 150, the storage 220, the storage 390, or an external source). The processing device 140A may retrieve the images from the storage device.

In 502, the processing device 140A (e.g., the identification module 402, the processing circuits of the processor 210) may identify one or more feature points relating to the ROI from the reference image.

As used herein, a feature point may refer to a representative point of the ROI which can be used to measure the physiological motion of the ROI. For example, if the ROI is a lung of a patient, the feature point(s) relating to the lung in the reference image may include one or more bifurcations of a blood vessel or a trachea in the lung. As another example, if the ROI is the heart of a patient, the feature point(s) relating to the heart in the reference image may include one or more pairs of feature points. Each pair of feature points may include an inner point on an endocardium (i.e., an inner border of the myocardium) of the heart and a corresponding outer point on an epicardium (i.e., an outer border of the myocardium) of the heart. As used herein, an inner point and an outer point that are located along (or nearly located along) a same straight line passing through a center of the heart (e.g., a center of gravity of the left ventricle) may be regarded as being corresponding to each other. For example, a center of the heart in a short axis CMRI image may refer to a center of the endocardium or the epicardium of the heart in the short axis CMRI image.

In some embodiments, the feature point(s) may be identified from the reference image according to a user input. For example, via a user interface implemented on, e.g., a terminal 130 or a mobile device 300, a user may manually mark one or more feature points in the reference image. Alternatively, the feature point(s) may be identified from the reference image automatically by the processing device 140A. Alternatively, the feature point(s) may be identified from the reference image by the processing device 140A semi-automatically. For example, the feature point identification may be performed by the processing device 140A based on an image analysis algorithm in combination with user intervention. Exemplary user interventions may include providing a parameter relating to the image analysis algorithm, providing a position parameter relating to a feature point, making an adjustment to or confirming a preliminary feature point identified by the processing device 140A, providing instructions to cause the processing device 140A to repeat or redo the feature point identification, etc.

For illustration purposes, an exemplary process for identifying an inner point and a corresponding outer point of the heart from a reference mage is provided hereinafter. In some embodiments, the processing device 140A may segment an endocardium and an epicardium of the heart from the reference image. For example, a user may manually annotate the endocardium and the epicardium from the reference image via a user interface, and the processing device 140A may segment the endocardium and the epicardium according to the user annotation. As another example, the endocardium and the epicardium of the myocardium may be segmented by the processing device 140A automatically according to an image analysis algorithm (e.g., an image segmentation algorithm). Alternatively, the endocardium and the epicardium may be segmented by the processing device 140A semi-automatically based on an image analysis algorithm in combination with information provided by a user. Exemplary information provided by the user may include a parameter relating to the image analysis algorithm, a position parameter relating to the endocardium and the epicardium, an adjustment to or confirmation of a preliminary endocardium and/or a preliminary epicardium generated by the processing device 140A, etc.

After the endocardium and the epicardium of the myocardium are segmented, the processing device 140A may identify the inner point at the endocardium and the corresponding outer point at the epicardium from the reference image based on the positions of the endocardium and the epicardium. Similar to the determination of the endocardium and the epicardium as described above, the inner point and the corresponding outer point may be determined according to a use annotation regarding the inner point and the corresponding outer point. Alternatively, the inner point and the corresponding outer point may be determined automatically based on the positions of the endocardium and the epicardium by the processing device 140A. For example, the processing device 140A may determine an intersection point between the epicardium and a line connecting the inner point and the heart center, and designate the intersection point as the corresponding outer point of the inner point. As another example, the processing device 140A may utilize a Laplace equation between the endocardium and epicardium to determine the inner point and the corresponding outer point. In some embodiments, the processing device 140A may determine a circle (denoted as C1) that has a central point coincident with the heart center and passes through the inner point. Using the Laplace equation, the processing device 140A may further determine one or more candidate circles by expending the radius of the circle C1. For each candidate circle, the processing device 140A may determine an intersection point between the candidate circle and a normal of the circle C1 at the inner point. The intersection point of a certain candidate circle that is located at the epicardium may be determined as the outer point corresponding to the inner point.

In some embodiments, the processing device 140A may identify a plurality of pairs of inner point and outer point from the reference image of the heart. For example, the processing device 140A may segment the heart into a plurality of sub-regions, each of which may include a specific artery. For each sub-region, an inner point and a corresponding outer point may be identified from the sub-region, wherein the identified inner point and the outer point may be used in analyzing the physiological condition of the sub-region.

In 503, the processing device 140A (e.g., the motion field determination module 403, the processing circuits of the processor 210) may determine a motion field of the feature point(s) from the reference motion phase to the target motion phase using a motion prediction model.

The motion field of the feature point(s) may include one or more motion vectors, each of which corresponds to one of the feature point(s). A motion vector of a feature point may be used to describe a motion of the feature point between the reference motion phase and the target motion phase. Merely by way of example, a location of a certain feature point in the reference image may be represented as a first coordinate (X1, Y1, Z1). The certain feature point may have a corresponding point in the target image that represents a same physical point of the ROI as the certain feature point. The location of the point corresponding to the certain feature point may be represented as a second coordinate (X2, Y2, Z2). The motion vector of the certain feature point from the reference motion phase to the target motion phase may be (Ux, Uy, Uz), wherein Ux, Uy, and Uz may be equal to (X1-X2), (Y1-Y2), and (Z1-Z2), respectively. In some embodiments, there may be a plurality of feature points relating to the ROI. The motion field may include motion vector(s) of all or a portion of the plurality of feature points between the reference and target motion phases.

Figure 10:
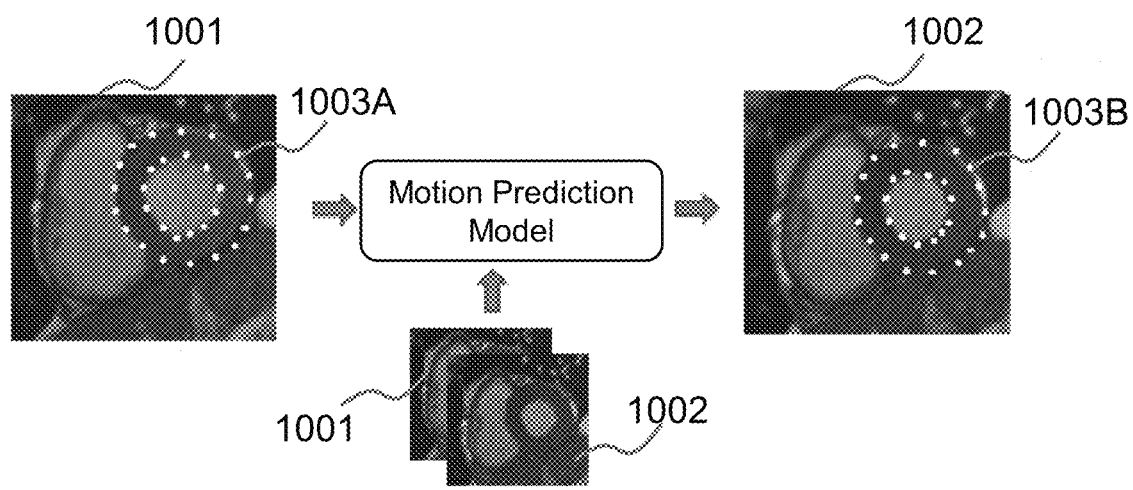
FIG. 10 illustrates a schematic diagram illustrating an exemplary application of a motion prediction model according to some embodiments of the present disclosure.

As used herein, a motion prediction model may refer to a neural network model configured to receive a pair of images corresponding to two different motion phases of the ROI, and output a motion field between (or with respect to) the pair of images. For example, as shown in FIG. 10, a reference image 1001 and a target image 1002 corresponding to two cardiac phases may be inputted into the motion prediction model, and the motion prediction model may output a motion field from the reference image 1001 to the target image 1002. The motion field outputted by the motion prediction model may include a motion vector of each point in the reference image 1001 from the reference motion phase to the target motion phase. A motion vector of a feature point 1003A in the reference image 1001 may be determined based on the motion field of the entire reference image 1001 by the processing device 140A. Optionally, a feature point 1003B corresponding to the feature point 1003A may be identified in the target image 1002 based on the motion vector of the feature point 1003A.

In some embodiments, the motion prediction model may be obtained from one or more components of the imaging system 100 or an external source via a network (e.g., the network 120). For example, the motion prediction model may be previously trained by a computing device (e.g., the processing device 140B), and stored in a storage device (e.g., the storage device 150, the storage 220, and/or the storage 390) of the imaging system 100. The processing device 140A may access the storage device and retrieve the motion prediction model. In some embodiments, the motion prediction model may be generated according to a machine learning algorithm. The machine learning algorithm may include but not be limited to an artificial neural network algorithm, a deep learning algorithm, a decision tree algorithm, an association rule algorithm, an inductive logic programming algorithm, a support vector machine algorithm, a clustering algorithm, a Bayesian network algorithm, a reinforcement learning algorithm, a representation learning algorithm, a similarity and metric learning algorithm, a sparse dictionary learning algorithm, a genetic algorithm, a rule-based machine learning algorithm, or the like, or any combination thereof.

In some embodiments, the motion prediction model may be trained by a computing device (e.g., the processing device 140B or an external processing device) using a supervised learning algorithm (or referred to as a supervised training process or technique). Merely by way of example, the computing device may obtain one or more annotated training samples. Each of the annotated training sample(s) may include a first annotated image of a sample ROI corresponding to a first motion phase, a second annotated image of the sample ROI corresponding to a second motion phase, and a sample motion field between (or with respect to) the first annotated image and the second annotated image. For an annotated training sample, the first annotated image may be annotated with one or more first sample feature points relating to the sample ROI, and the second annotated image may be annotated with one or more second sample feature points corresponding to the first sample feature points. The sample motion field of the annotated training sample may be determined based on the first annotated image and the second annotated image according to an image registration technique. In some embodiments, the sample ROI may be of a same type as the ROI. As used herein, two ROIs are deemed to be of a same type when they belong to a same type of organ or tissue. The first and second annotated images of each annotated training sample may be of a same type of image as the reference image and the target image as described above. As used herein, two images are deemed to be of a same type when they are generated using a same type of imaging technique (e.g., an MRI technique, a CT technique). The first and second sample feature points of each annotated training sample may be annotated manually, automatically, or semi-automatically according to a feature point identification technique as described elsewhere in this disclosure (e.g., 502 and the relevant descriptions).

The computing device may further generate the motion prediction model by training a first preliminary model using the annotated training sample(s) according to a supervised learning technique. Merely by way of example, the first and second annotated images of each annotated training sample may be inputted into the first preliminary model, which may output a predicted motion field from the first annotated image to the second annotated image. The computing device may determine a value of a first loss function based on the predicted motion field and the known sample motion field of each annotated training sample. For example, the first loss function may measure the difference(s) between the predicted motion field and the sample motion field of the annotated training sample(s). Alternatively, for each training sample, the computing device may determine a predicted motion field and an actual motion field of the first sample feature point(s) from the first motion phase to the second motion phase based on the predicted motion field and the sample motion field of the entire first annotated image, respectively. The first loss function may measure a difference between the predicted and actual motion fields of the first sample feature point(s) of each annotated training sample. The first preliminary model may be iteratively trained to minimize the first loss function. The trained model of the first preliminary model may be designated as the motion prediction model.

In some embodiments, the motion prediction model may be trained by a computing device (e.g., the processing device 140B or an external processing device) using an unsupervised learning algorithm. For example, the motion prediction model may be trained using one or more unannotated training samples. More descriptions regarding the generation of the motion prediction model according to an unsupervised learning technique may be found elsewhere in the present disclosure. See, e.g., FIG. 6 and relevant descriptions thereof.

In 504, the processing device 140A (e.g., the physiological condition determination module 404, the processing circuits of the processor 210) may determine a physiological condition of the ROI based on the motion field.

The physiological condition of the ROI may indicate a health status of the ROI. For example, based on the motion field, the processing device 140A may determine a value of a biological parameter indicating the physiological condition of the ROI, an analyzing result of the physiological condition of the ROI (e.g., a determination as to whether the value of a biological parameter of the ROI is within a normal region, a predicted risk that the ROI has a certain disease, a treatment suggestion regarding the ROI), or the like, or any combination thereof.

For illustration purposes, the following descriptions are described with reference to the determination of a physiological condition of the heart of a patient, and not intended to limit the scope of the present disclosure. In some embodiments, the processing device 140A may determine the physiological condition of the heart directly based on the motion field. Merely by way of example, the feature point(s) determined in 502 may include a plurality feature points relating to the heart. The processing device 140A may determine a motion parameter of the whole heart to indicate the physiological condition of the whole heart. The motion parameter may be, for example, an average value, a maximum value, a minimum value, or the like, of all or a portion of the motion vectors of the feature points. The processing device 140A may determine if the motion parameter is within a normal range. A motion parameter out of the normal range may indicate that the heart is in an abnormal state (e.g., having a myocardial dysfunction). As another example, the feature points may be located at different sub-regions of the heart. The processing device 140A may determine a physiological condition of a certain sub-region by, for example, analyzing a motion parameter of the certain sub-region based on the motion vector(s) of the feature point(s) in the certain sub-region. Alternatively, the processing device 140A may determine a physiological condition of the heart by comparing the motion parameters of different sub-regions. For example, if a motion parameter of a certain sub-region is greater than an average motion parameter of all the sub-regions by a threshold, the certain sub-region may be considered as in an abnormal state.

In some embodiments, the processing device 140A may determine a biological parameter of the heart based on the motion field, and analyze the physiological condition of the heart according to the biological parameter. For example, a strain value relating to the heart may be determined for strain analysis. Strain, also be referred to as myocardial contractility, is a metric for quantifying myocardial dysfunction in patients. As described in connection with 502, the feature point(s) relating to the heart may include one or more pairs of feature points, each of which includes an inner point and a corresponding outer point. In some embodiments, based on the motion vectors of a pair of inner point and outer point located at a certain sub-region of the heart, the processing device 140A may determine a strain value of the certain sub-region.

Figure 9A:
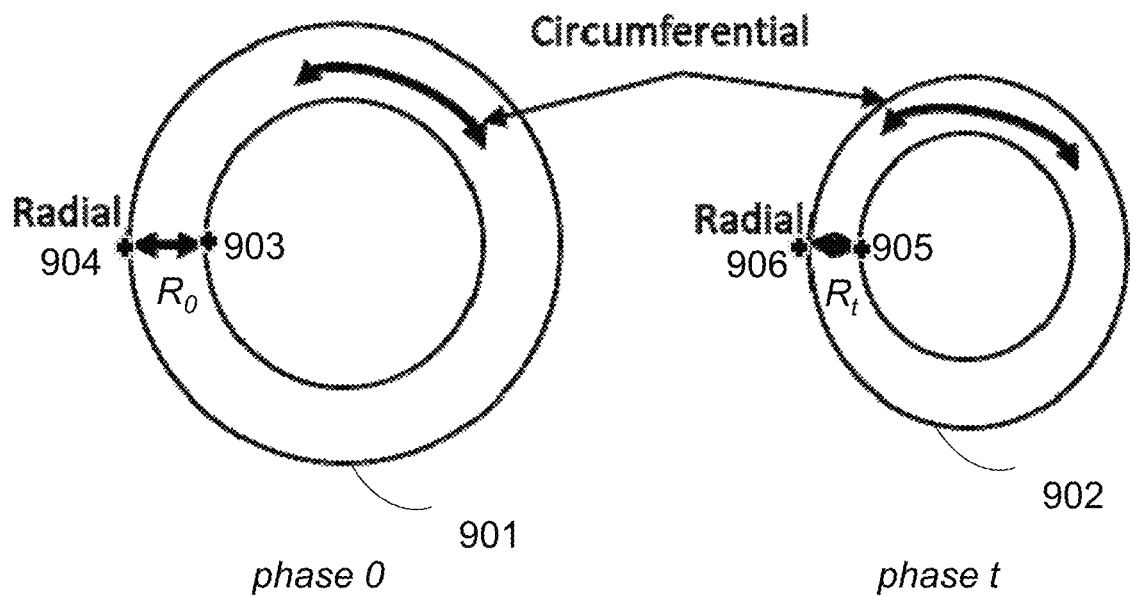
FIG. 9A illustrates schematic diagrams illustrating exemplary short-axis CMRI images according to some embodiments of the present disclosure.

FIG. 9A is a schematic diagram illustrating an exemplary reference image 901 and a target image 902 of a heart according to some embodiments of the present disclosure. The reference image 901 and the target image 902 may be short-axis CMRI images corresponding to Phase 0 and Phase t, respectively. A pair of feature points located at a first sub-region of the heart, including an inner point 903 and a corresponding outer point 904, may be identified from the reference image 901. A strain value in the radial direction (also be referred to as a radical strain value) and a strain value in the circumferential direction (also referred to as a circumferential strain value) of the first sub-region may be determined based on the motion vectors of the inner point 903 and the outer point 904.

Merely by way of example, the processing device 140A may determine a distance $R_0$ between the inner point 903 and the outer point 904 in the Phase 0 by analyzing the reference image 901. The processing device 140A may also determine a distance $R_t$ between the inner point 903 and the outer point 904 in the Phase t based on the motion vectors of the inner point 903 and the outer point 904. For example, an inner point 905 corresponding to the inner point 903 and an outer point 906 corresponding to the outer point 904 may be identified in the target image 902 based on the motion vectors of the inner point 903 and the outer point 904, respectively. The distance between the inner point 905 and the outer point 906 may be determined as the distance $R_t$. Further, the processing device 140A may determine a radial strain value $\varepsilon_R$ and/or a circumferential strain value $\varepsilon_C$ of the first sub-region based on $R_0$ and $R_t$ according to Equations (1) and (2), respectively, as below:

$$\varepsilon_R \approx \frac{R_t - R_0}{R_0}, \qquad (1)$$

$$\varepsilon_C \approx 0.5 \cdot \frac{R_t^2 - R_0^2}{R_0^2}. \qquad (2)$$

Figure 9B:
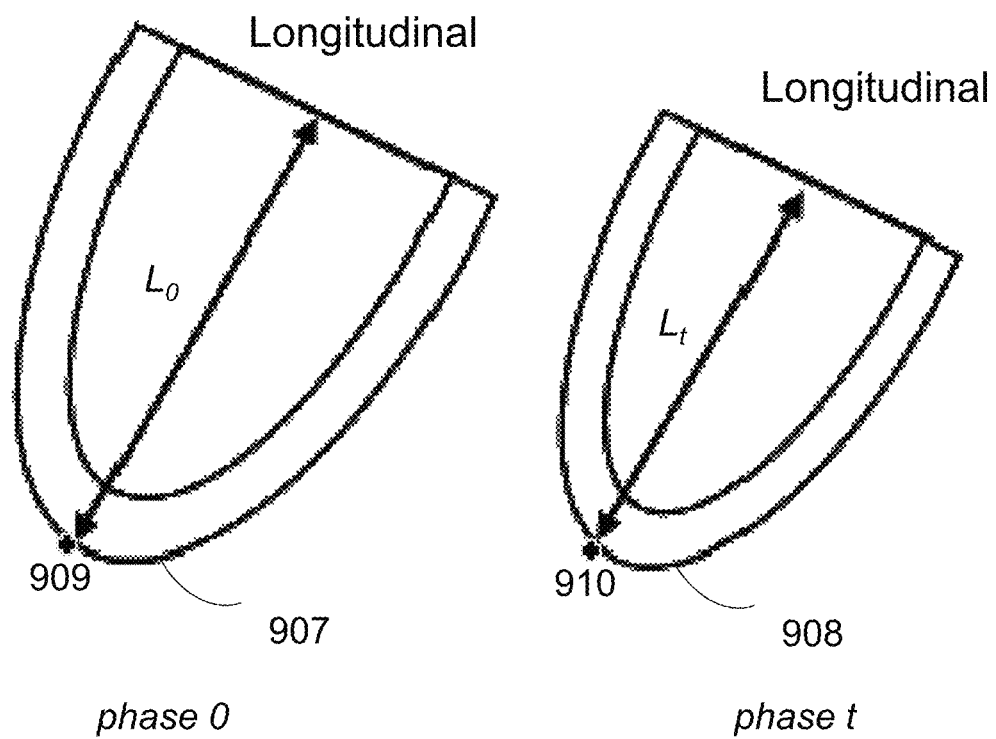
FIG. 9B illustrates schematic diagrams illustrating exemplary long-axis CMRI images according to some embodiments of the present disclosure.

FIG. 9B is a schematic diagram illustrating an exemplary reference image 907 and a target image 908 of a heart according to some embodiments of the present disclosure. The reference image 907 and the target image 908 may be long-axis CMRI images corresponding to Phase 0 and Phase t, respectively. An outer point 909 located at a second sub-region may be identified from the reference image 907. A strain value in the longitudinal direction (also be referred to as a longitudinal strain value) of the second sub-region may be determined based on the motion vector of the outer point 909. Merely by way of example, the processing device 140A may determine a distance $L_0$ between the outer point 909 and a reference plane on the upper portion of the heart in the Phase 0 based on the reference image 907. The processing device 140A may also determine an outer point 910 in the target image 908 based on the motion vector of the outer point 909, wherein the outer point 910 may correspond to the inner point 909. The processing device 140A may then determine a distance $L_t$ between the outer point 910 and a reference plane on the upper portion of the heart in the Phase t. Further, the processing device 140A may determine a longitudinal strain value $\varepsilon_L$ of the second sub-region based on $L_0$ and $L_t$ according to Equation (3) as below:

$$\varepsilon_L \approx \frac{L_t - L_0}{L_0}. \qquad (3)$$

After the strain value of the certain sub-region is determined, the processing device 140A may determine the physiological condition of the certain sub-region according to the determined strain value. Merely by way of example, if the strain value is out of a normal strain range, the certain sub-region may be considered as in an abnormal condition. In some embodiments, the strain values of a plurality of sub-regions of the heart may be determined. The strain values of the sub-regions may be compared with each other in order to identify an abnormal sub-region (e.g., a sub-region having a strain value greater than an average strain value by a threshold). As another example, the processing device 140A may determine an overall strain value of the whole heart based on the stain values of different sub-regions, and determine the physiological condition of the whole heart based on the overall strain value.

In some embodiments, in 501, at least three images corresponding to at least three motion phases may be obtained. The at least three images may form a plurality of pairs of images. For example, 10 CMRI images, from the ED phase to the ES phase or from the ES phase to the ED phase, may be obtained. Every two images corresponding to consecutive cardiac phases may form a pair of images. Alternatively, any two different images corresponding to different cardiac phases may form a pair of images. For each pair of images, the processing device 140A may perform operations 502 and 503 to determine a corresponding motion field. The processing device 140A may determine the physiological condition of the ROI based on the motion fields. Merely by way of example, a change in the motion fields over time may be determined to evaluate the physiological condition of the ROI.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 500 may be accomplished with one or more additional operations not described and/or without one or more of the operations discussed above. For example, the process 500 may include an additional operation to transmit the physiological condition to a terminal device (e.g., a terminal device 130 of a doctor) for display.

Figure 6:
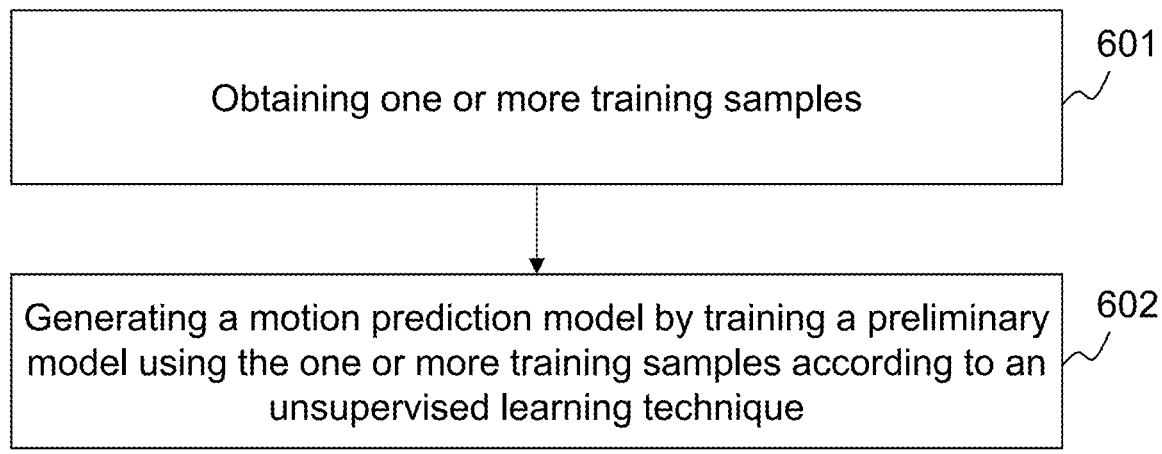
FIG. 6 is a flowchart illustrating an exemplary process for generating a motion prediction model using an unsupervised learning technique according to some embodiments of the present disclosure.

FIG. 6 is a flowchart illustrating an exemplary process for generating a motion prediction model using an unsupervised learning technique according to some embodiments of the present disclosure. In some embodiments, process 600 may be executed by the imaging system 100. For example, the process 600 may be implemented as a set of instructions (e.g., an application) stored in a storage device (e.g., the storage device 150, the storage 220, and/or the storage 390). In some embodiments, the processing device 140B (e.g., the processor 210 of the computing device 200, the CPU 340 of the mobile device 300, and/or one or more modules illustrated in FIG. 4B) may execute the set of instructions and may accordingly be directed to perform the process 600. Alternatively, the process 600 may be performed by a computing device of a system of a vendor that provides and/or maintains such motion prediction model, wherein the system of the vendor is different from the imaging system 100. For illustration purposes, the following descriptions are described with reference to the implementation of the process 600 by the processing device 140B, and not intended to limit the scope of the present disclosure.

In 601, the processing device 140B (e.g., the acquisition module 405, the interface circuits of the processor 210) may obtain one or more training samples.

Each training sample may include an image A (or also be referred to as a first image) and an image B (or also referred be to as a second image) indicative of a physiological motion of a sample ROI, wherein the images A and B may correspond to a first motion phase and a second motion field of the sample ROI, respectively. As used herein, the sample ROI of a training sample may refer to an ROI of a sample subject (e.g., a sample patient) that is used in training the motion prediction model.

In some embodiments, the sample ROI of each training sample may be of the same type as the ROI as described in connection with FIG. 5. The images A and B of each training sample may be of the same type as the reference image and the target image as described in connection with FIG. 5. For example, the motion prediction model may be used in the process 500 to determine a physiological motion of the heart of a patient between two cardiac phases based on two PET images of the heart corresponding to the two cardiac phases. In such cases, for each training sample, the sample ROI may be the heart of a sample patient, and the images A and B may be PET images of the heart of the sample patient corresponding to different cardiac phases.

In some embodiments, the images A and B of the training sample(s) may be obtained in a similar manner as acquiring the images of the ROI as described in connection with 501. For example, the images A and B of a training sample may be obtained by an image acquisition device via scanning a sample patient. Alternatively, the images A and B of a training sample may be retrieved from a storage device (e.g., the storage device 150 or an external source) that stores the images A and B.

In 602, the processing device 140B (e.g., the model generation module 406, the processing circuits of the processor 210) may generate the motion prediction model by training a preliminary model using the training sample(s) according to an unsupervised learning technique.

In some embodiments, the processing device 140B may train the preliminary model by minimizing a loss function. A loss function of a model may be used to evaluate the accuracy and reliability of the model, for example, the smaller the loss function is, the more reliable of the model is. When the loss function of the preliminary model is minimized, the processing device 140B may designate at least a portion of the trained model as the motion prediction model. In some embodiments, the processing device 140B may train the preliminary model by performing one or more operations in process 700 described in FIG. 7.

Figure 11:
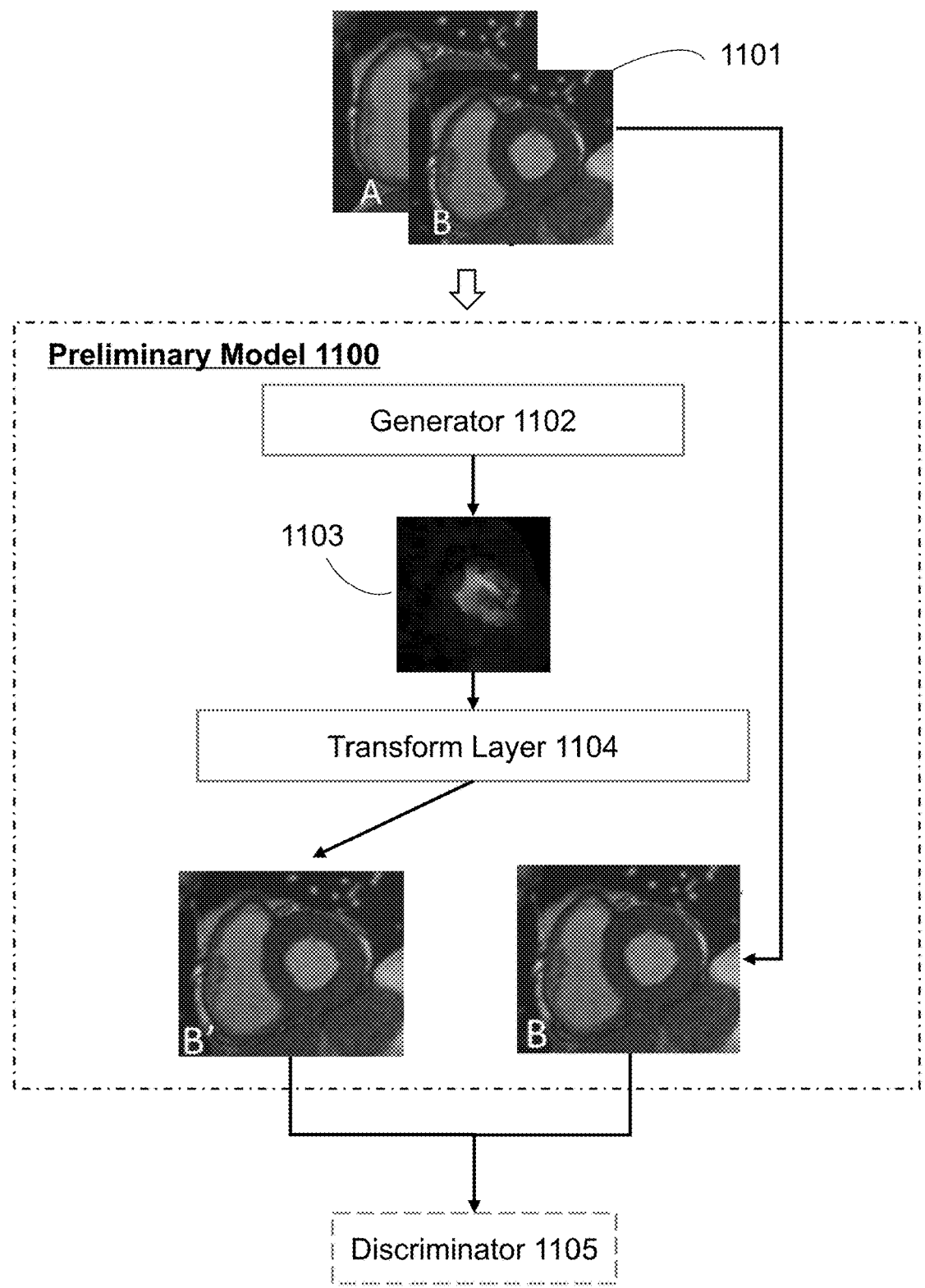
FIG. 11 is a schematic diagram illustrating an exemplary preliminary model according to some embodiments of the present disclosure.

For illustration purposes, an exemplary preliminary model 1100 according to some embodiments of the present disclosure is illustrated in FIG. 11. As illustrated in FIG. 11, the preliminary model 1100 may include a generator 1102 and a transformation layer 1104. One or more training samples, each of which includes a pair of CMRI images A and B (also referred to as an image pair (A, B)) corresponding to different cardiac phases, may be used to train the preliminary model 1100 in order to generate a first trained model.

Taking a training sample 1101 shown in FIG. 11 as an example, the generator 1102 may be configured to predict a first motion field 1103 from the image A to the image B. The transformation layer 1104 may be configured to warp the image A according to the first motion field 1103 to generate an image B', which may be regarded as a predicted image B (or also be referred to as a predicted second image). Merely by way of example, each pixel (or voxel) in the image A may be transformed according to the motion vector of the pixel (or voxel), so as to generate the image B' of the training sample 1101. In some embodiments, the generator 1102 and the transformation layer 1104 may be any neural network component that can realize their respective functions. Merely by way of example, the generator 1102 may be a convolutional neural network (CNN). The transformation layer 1104 may be a spatial transformation network.

In some embodiments, the loss function of the preliminary model 1100 may relate to a first difference between the image B and the image B' of each training sample. For example, the training sample(s) may include a plurality of training samples. The loss function may be used to measure an overall level (e.g., an average value) of the first differences of the training samples. The loss function may be minimized in the model training so that the first differences between the images B and B' of the training samples may be minimized locally or globally. As used herein, a difference between two images may be measured by any metrics for measuring a similarity degree or a difference between the two images. Merely by way of example, the difference between two images may be determined based on an image similarity algorithm, including a peak signal to noise ratio (PSNR) algorithm, a structural similarity (SSIM) algorithm, a perceptual hash algorithm, a cosine similarity algorithm, a histogram-based algorithm, a Euclidean distance algorithm, or the like, or any combination thereof.

Optionally, for each training sample, the processing device 140B may further determine a second motion field from the image B to the image A of the training sample using the preliminary model 1100. For example, for the training sample 1101, the image pair (A, B) may be transformed into an image pair (B, A), which may be inputted into the generator 1102 to obtain the second motion field of the training sample 1101. The processing device 140B may further determine an opposite motion field (or referred to as a reversed motion field) of the second motion field of the training sample 1101. Theoretically, if the generator 1102 is accurate enough (e.g., having an accuracy higher than a threshold), the first motion field 1103 may be substantially equal to an opposite motion field of the second motion field. A second difference between the opposite motion field and the first motion field 1103 may be determined to indicate the accuracy of the generator 1102. In some embodiments, the second difference of each training sample may be taken into consideration in training the preliminary model 1100. For example, a motion consistency loss may be determined to measure an overall level of the second difference(s) of the training sample(s) and incorporated into the loss function of the preliminary model 1100. This may improve the consistency and reliability of the first trained model.

In some embodiments, the preliminary model 1100 may further include a discriminator 1105 as shown in FIG. 11. Such preliminary model 1100 including the discriminator 1105 may also be referred to as a generative adversarial network (GAN) model. For the training sample 1101, the discriminator 1105 may be configured to receive the images B and B' of the training sample 1101, and discern which one is a real image to generate a discrimination result between the images B and B'. For example, the discriminator result may include a determination as to whether the image B is a real image, a probability that the image B is a real image, a determination as to whether the image B' is a real image, a probability that the image B' is a real image, or the like, or any combination thereof. In some embodiments, the discriminator 1105 may be any neural network component that can realize its function. Merely by way of example, the discriminator 1105 may be an image classifier, a patch GAN discriminator, etc. In some embodiments, the loss function of a preliminary model 1100 that includes the discriminator 1105 may be determined based on the first difference, the discrimination result, and optionally the second difference of each training sample. In some embodiments, the loss function of a preliminary model 1100 that includes the discriminator 1105 may be a GAN loss.

Figure 12:
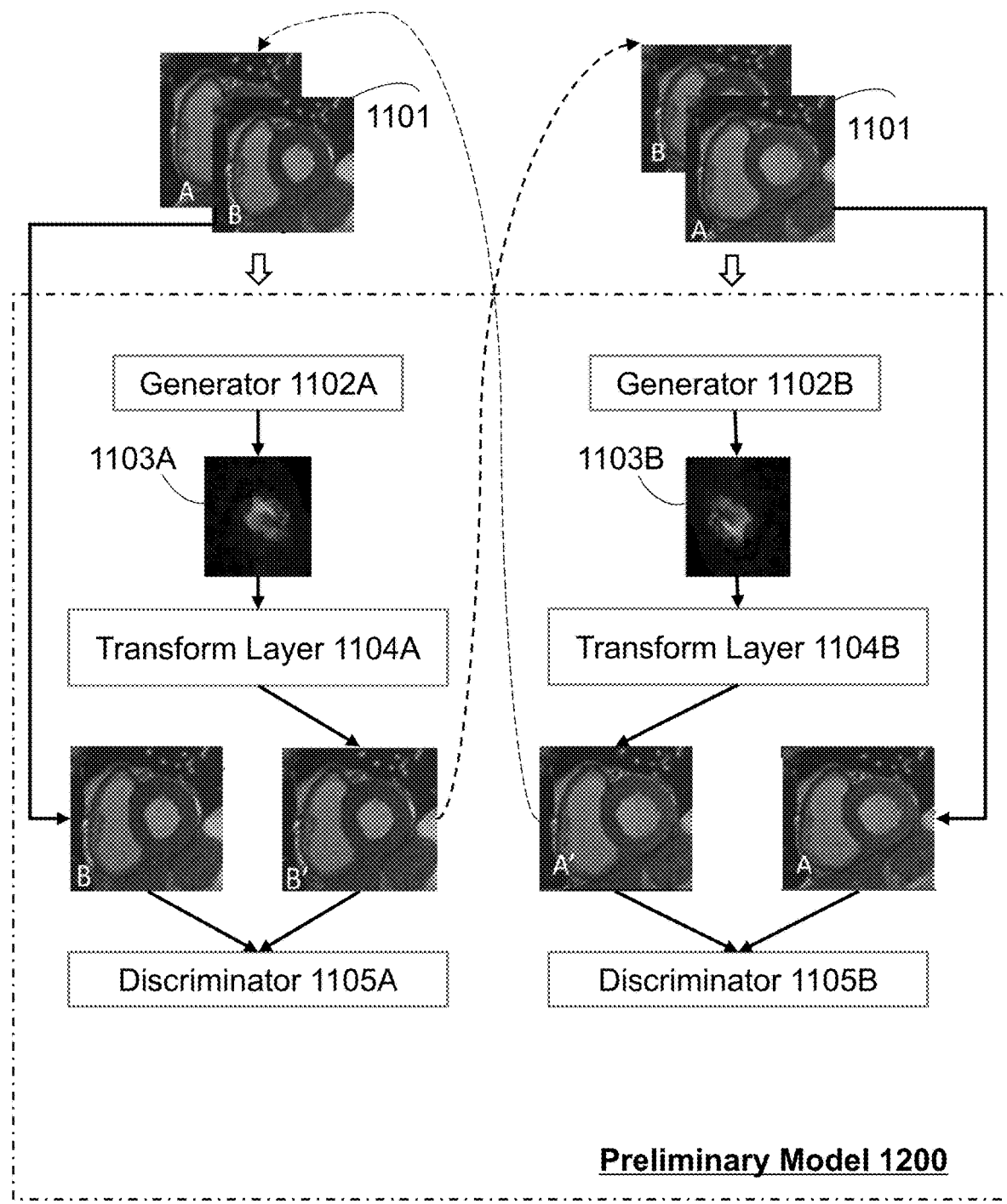
FIG. 12 is a schematic diagram illustrating another exemplary preliminary model according to some embodiments of the present disclosure.

In some embodiments, the preliminary model may be a preliminary model 1200 as illustrated in FIG. 12. The preliminary model 1200 may be trained using the same or similar training sample(s) of the preliminary model 1100 to generate a second trained model. The preliminary model 1200 may include a forward pipeline (the left portion illustrated in FIG. 12) and a backward pipeline (the right portion illustrated in FIG. 12). Each of the forward and backward pipelines may include the same or similar configuration as the preliminary model 1100 as described in connection with FIG. 11. For example, as shown in FIG. 12, the forward pipeline may include a generator 1102A, a transformation layer 1104A, and a discriminator 1105A. The backward pipeline may include a generator 1102B, a transformation layer 1104B, and a discriminator 1105B.

For the training sample 1101, the image pair (A, B) and the image pair (B, A) may be inputted into the forward pipeline and the backward pipeline, respectively. The forward pipeline may be used to generate an image B' (i.e., a predicted image B) by warping the image A according to the image B. For example, the generator 1102A may predict a motion field 1103A from the image A to the image B of the training sample 1101. The transformation layer 1104A may generate the image B' by warping the image A according to the motion field 1103A. The discriminator 1105A may be configured to generate a discrimination result between the images B and B'. The backward pipeline may be used to generate an image A' (i.e., a predicted image A) by warping the image B according to the image A. For example, the generator 1102B may predict a motion field 1103B from the image B to the image A of the training sample 1101. The transformation layer 1104B may generate the image A' by warping the image B according to the motion field 1103B. The discriminator 1105B may be configured to generate a discrimination result between the images A and A'.

In some embodiments, the preliminary model 1200 may be trained to minimize a loss function of the preliminary model 1200. The loss function of the preliminary model 1200 may include a first component associated with the forward pipeline and/or a second component associated with the backward pipeline. Each of the first component and the second component may be similar to the loss function of the preliminary model 1100 as described in connection with FIG. 11. Taking the forward pipeline as an instance, the corresponding first component may relate to a first difference and a discrimination result between images B and B' of each training sample, and optionally a consistency motion loss.

In some embodiments, for the training sample 1101, the processing device 140B may further replace the image A in the image pair (A, B) with the image A' generated by the back pipeline to generate an image pair (A', B). The image pair (A', B) may be inputted into the forward pipeline to generate an image B" (or also referred be to as a third image) by warping the image A' according to the image B of the training sample 1101. In other words, the image A' may be generated by performing a backward transformation on the image B of the training sample 1101, and the image B" may be generated by performing a forward transformation on the image A' of the training sample 1101. Theoretically, if the preliminary model 1200 is accurate enough (e.g., having an accuracy higher than a threshold), the image B" may be substantially the same as the image B of the training sample 1101. A third difference between the images B and B" may be determined and taken into consideration in the training of the preliminary model 1200. For example, the loss function of the preliminary model 1200 may be determined based on the first component relating to the forward pipeline, the second component relating to the backward pipeline, the third difference of each training sample, or any combination thereof.

Additionally or alternatively, for the training sample 1101, the processing device 140B may replace the image B in the image pair (B, A) with the image B' generated by the forward pipeline to generate an image pair (B', A). The image pair (B', A) may be inputted in the backward pipeline to generate an image A" (or also referred be to as a fourth image) by wrapping the image B' according to the image A. Similar to the images B and B" as aforementioned, the images A and A" may be supposed to be substantially the same as each other. A fourth difference between the images A and A" may be determined and taken into consideration in the training of the preliminary model 1200. For example, the loss function of the preliminary model 1200 may be determined based on the first component, the second component, the third difference of each training sample, the fourth difference of each training sample, or any combination thereof.

In some embodiments, the training process of the preliminary model 1200 may be an iterative process. An error may accumulate in the iterative process, which may result in a drifting error and in turn a trained model having a low accuracy. By taking into consideration of the third difference and/or the fourth difference of each training sample, the drifting error may be eliminated or reduced, which, in turn, may improve the accuracy and reliability of the second trained model.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 600 may be accomplished with one or more additional operations not described and/or without one or more of the operations discussed above. For example, the process 600 may include an additional operation to store the motion prediction model in a storage device (e.g., the storage device 150, the storage 220, and/or the storage 390) for further use (e.g., in process 500).

In addition, the preliminary model exemplified above, such as the preliminary models 1100 and 1200, is merely provided for the purposes of illustration, and not intended to limit the scope of the present disclosure. In some embodiments, one or more components of the preliminary model may be omitted and/or the preliminary model may include one or more additional components. For example, the discriminator 1105A and/or the discriminator 1105B of the preliminary model 1200 may be removed. Additionally or alternatively, two or more components of the preliminary model may be integrated into a single component. For example, the generator 1102A and the generator 1102B of the preliminary model 1200 may be integrated into a single generator.

In some embodiments, the generated motion prediction model may be utilized in image segmentation by the processing device 140B or another computing device (e.g., the processing device 140A). For example, the processing device 140B may obtain an annotated image of a sample ROI corresponding a third motion phase and unannotated image of the sample ROI corresponding a fourth motion phase. The third and fourth motion phases may be two different motion phases of the sample ROI. The annotated image may include an annotation of one or more first feature points relating to the sample ROI. The identification of the first feature point(s) in the annotated image may be performed according to a feature point identification technique as described elsewhere in this disclosure (e.g., 502 and the relevant descriptions). The processing device 140B may determine a motion field of the first feature point(s) from the third motion phase to the fourth motion phase by inputting the annotated image and the unannotated image into the motion prediction model. The motion field of the first feature point(s) may be determined in a similar manner as how the motion field of the feature point(s) of the reference image is determined as described in connection with 503. The processing device 140B may generate a second annotated image of the sample ROI corresponding the fourth motion phase based on the annotation of the first feature point(s) and the motion field of the first feature point(s). The second annotated image may include an annotation of one or more second feature point(s) corresponding to the first feature point(s). For example, for a certain first feature point, the processing device 140B may determine the coordinate of a corresponding second feature point in the unannotated image by transforming the coordinate of the certain first feature point according to the motion vector of the certain first feature point. The processing device 1406 may further generate an annotation of the determined second feature point corresponding to the certain first feature point. In this way, the ROI (e.g., the second feature point(s) of the ROI) may be segmented in the unannotated image and a segmented image (i.e., the second annotated image) may be generated.

Optionally, the annotated image and the second annotated image may be used in the training of a segmentation model. The segmentation model may be used to segment an ROI (e.g., the heart or a lung) from an image including the ROI. The segmentation model may be trained by a computing device (e.g., the processing device 140A or 140B) of the imaging system 100 or an external computing device. In some embodiments, the segmentation model may be trained using a supervised learning technique. To this end, a plurality of training images labeled with a sample ROI (e.g., by a bounding box) may be needed. The labeling of the sample ROI in the training images may be time-consuming and inefficient. The annotated image and the second annotated image may be used as an annotated training sample for training the segmentation model. This may mitigate the labeling effort, thus improving the training efficiency of the segmentation model.

In some embodiments, the trained model may include a trained discriminator, e.g., the one derived from the discriminator 1105. The trained discriminator may be utilized to evaluate the quality of the second annotated image. For example, the annotated image may be warped based on the motion field from the annotated image to the unannotated image. The warped annotated image and the unannotated image may be inputted into the trained discriminator, which may determine a discrimination result between the warped annotated image and the unannotated image. Optionally, the discrimination result may include a probability that the warped annotated image is a real image. For example, if the probability is greater than a threshold, it may suggest that the motion field from the annotated image to the unannotated image is reliable, which, in turn, may suggest that the quality of the second annotated image generated based on the motion field is reliable and qualified for training of the segmentation model. If the probability is smaller than the threshold, the second annotated image may be discarded.

Figure 7:
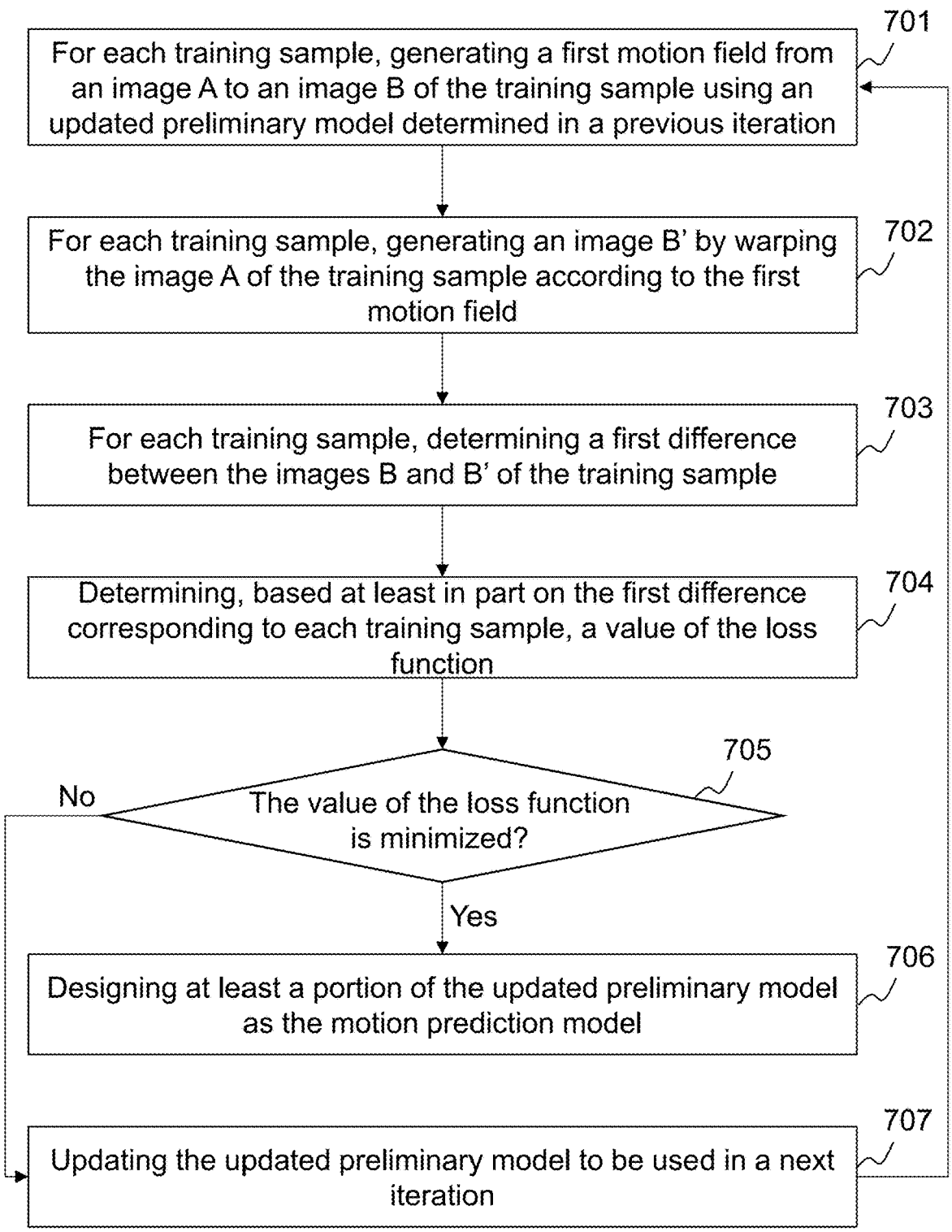
FIG. 7 is a flowchart illustrating an exemplary process for minimizing a loss function to generate a motion prediction model according to some embodiments of the present disclosure.

FIG. 7 is a flowchart illustrating an exemplary process for minimizing a loss function to generate a motion prediction model according to some embodiments of the present disclosure. In some embodiments, process 700 may be executed by the imaging system 100. For example, the process 700 may be implemented as a set of instructions (e.g., an application) stored in a storage device (e.g., the storage device 150, the storage 220, and/or the storage 390). In some embodiments, the processing device 140B (e.g., the processor 210 of the computing device 200, the CPU 340 of the mobile device 300, and/or one or more modules illustrated in FIG. 4B) may execute the set of instructions and may accordingly be directed to perform the process 700. Alternatively, the process 700 may be performed by a computing device of a system of a vendor that provides and/or maintains such motion prediction model, wherein the system of the vendor is different from the imaging system 100. For illustration purposes, the following descriptions are described with reference to the implementation of the process 700 by the processing device 140B, and not intended to limit the scope of the present disclosure.

As described in connection with FIG. 6, in some embodiments, the motion prediction model may be generated by training a preliminary model using one or more training samples. Each training sample may include a pair of images A and B corresponding to different motion phases of a sample ROI. In some embodiments, the preliminary model may include one or more model parameters having one or more initial values before model training. In the training of the preliminary model, the value(s) of the model parameter(s) of the preliminary model may be updated such that the loss function of the preliminary model may be minimized. In some embodiments, the training of the preliminary model may include one or more iterations. For illustration purposes, a current iteration of the iteration(s) is described in the following description. The current iteration may include one or more operations of process 700 illustrated in FIG. 7.

In 701, for each training sample, the processing device 140B (e.g., the model generation module 406, the processing circuits of the processor 210) may generate a first motion field from the image A to the image B of the training sample using an updated preliminary model determined in a previous iteration.

In 702, for each training sample, the processing device 140B (e.g., the model generation module 406, the processing circuits of the processor 210) may generate an image B' by warping the image A of the training sample according to the first motion field using the updated preliminary model.

For example, the preliminary model may be the preliminary mode 1100 as illustrated in FIG. 11 or the preliminary model 1200 illustrated in FIG. 12. The updated preliminary models of the preliminary model 1100 and the preliminary model 1200 determined in the previous iteration may be denoted as a model M1 and a model M2, respectively, for the convenience of description. The image pair (A, B) of a training sample may be inputted into the model M1 or the model M2 to obtain the image B'.

In 703, for each training sample, the processing device 140B (e.g., the model generation module 406, the processing circuits of the processor 210) may determine a first difference between the image B' and the image B of the training sample.

The first difference between the images B' may be determined based on an algorithm for measuring a similarity degree or a difference between two images. More descriptions regarding the determination of the first difference of a training sample may be found elsewhere in the present disclosure. See, e.g., operation 602 and relevant descriptions thereof.

In 704, the processing device 140B (e.g., the model generation module 406, the processing circuits of the processor 210) may determine a value of the loss function based at least in part on the first difference corresponding to each training sample.

In some embodiments, the training sample(s) may include a plurality of training samples. The loss function may be configured to measure an overall level (e.g., an average value) of the first differences of the training samples. In some embodiments, the value of the loss function may be determined based on the first differences of the training samples as well as one or more other metrics. Merely by way of example, the loss function of the preliminary model 1100 may incorporate a motion consistency loss as described in connection with FIG. 6. As another example, the loss function of the preliminary model 1200 may be associated with a third difference and/or a fourth difference of each training sample as described in FIG. 6.

In 705, the processing device 140B (e.g., the model generation module 406, the processing circuits of the processor 210) may determine whether the value of the loss function is minimized in the current iteration.

For example, the value of the loss function may be regarded as being minimized if the value of the loss function obtained in the current iteration is less than a predetermined threshold. As another example, the value of the loss function may be regarded as being minimized if a certain count of iterations is performed, or the loss function converges such that the differences of the values of the loss function obtained in consecutive iterations are within a threshold, etc.

In response to a determination that the value of the loss function is minimized, the process 700 may proceed to 706, in which the processing device 140B (e.g., the model generation module 406, the processing circuits of the processor 210) may design at least a portion of the updated preliminary model in the current iteration as the motion prediction model. For example, the updated generator derived from the generator 1102 in the model M1 may be regarded as a trained generator and designated as the motion prediction model. As another example, the updated generator derived from the generator 1102A or 1102B in the model M2 may be regarded as a trained generator and designated as the motion prediction model.

In response to a determination that the value of the loss function is not minimized in the current iteration, the process 700 may proceed 707, in which the processing device 140B (e.g., the model generation module 406, the processing circuits of the processor 210) may further update the updated preliminary model to be used in a next iteration.

For example, the processing device 140B may update the value(s) of the model parameter(s) of the updated preliminary model based on the value of the loss function according to, for example, a backpropagation algorithm. The processing device 140B may perform the next iteration until the value of the loss function is minimized. After the value of the loss function is minimized in a certain iteration, at least a portion of the updated preliminary model in the certain iteration may be designated as the motion prediction model.

It should be noted that the above descriptions regarding the process 700 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the order of the process 700 may not be intended to be limiting. Additionally or alternatively, the process 700 may be accomplished with one or more additional operations not described and/or without one or more of the operations discussed above. For example, the processing device 140B may further test the motion prediction model using a set of testing samples to determine whether a testing condition is satisfied. If the testing condition is not satisfied, the process 700 may be performed again to further train the preliminary model.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
   at least one storage device including a set of instructions for physiological motion measurement; and
   at least one processor configured to communicate with the at least one storage device, wherein when executing the set of instructions, the at least one processor is configured to direct the system to perform operations including:
   acquiring a reference image of a region of interest (ROI) corresponding to a reference motion phase of the ROI and a target image of the ROI corresponding to a target motion phase of the ROI, the target motion phase being different from the reference motion phase;
   identifying one or more feature points relating to the ROI from the reference image;
   determining, based on the reference image, a first distance between a first feature point and a second feature point of the one or more feature points, the first feature point and the second feature point being in the reference image corresponding to the reference motion phase;
   determining a motion field of the first feature point and the second feature point from the reference motion phase to the target motion phase using a motion prediction model, wherein an input of the motion prediction model includes at least the reference image and the target image;
   determining, based on the motion field, a second distance between a third feature point in the target image, corresponding to the first feature point, and a fourth feature point in the target image, corresponding to the second feature point; and
   determining, based on the first distance and the second distance, a physiological condition of the ROI, wherein the motion prediction model is generated by performing an iteration operation for training a preliminary model using at least one training sample, each of the at least one training sample including a first sample image and a second sample image indicative of a physiological motion of a sample region of interest (ROI), the first sample image corresponding to a first motion phase of the sample ROI, and the second sample image corresponding to a second motion phase of the sample ROI, the iteration operating including one or more iterations, at least one of the one or more iterations including:
   for each of the at least one training sample,
   generating a first motion field from the first sample image to the second sample image using an updated preliminary model determined in a previous iteration;
   generating a predicted second sample image according to the first motion field; and
   determining a first difference between the predicted second sample image and the second sample image of the training sample;
   determining, based at least in part on the first difference corresponding to each of the at least one training sample, a value of a loss function; and
   updating the updated preliminary model to be used in a next iteration based on the value of the loss function.

2. The system of claim 1, wherein the ROI includes at least one of a heart, a lung, an abdomen, a chest, a stomach of a subject.

3. The system of claim 1, wherein
   the ROI is a heart,
   the first feature point relating to the heart in the reference image includes an inner point on an endocardium of the heart, and
   the second feature point relating to the heart in the reference image includes a corresponding outer point on an epicardium of the heart.

4. The system of claim 3, wherein to identify the inner point and the corresponding outer point from the reference image, the at least one processor is further configured to direct the system to perform additional operations including:
   segmenting, from the reference image, the endocardium and the epicardium; and
   identifying, based on positions of the endocardium and the epicardium, the inner point and the corresponding outer point from the reference image.

5. The system of claim 1, the ROI comprising a heart, wherein the motion field includes a motion vector of the first feature point and a motion vector of the second feature point, and to determine a physiological condition of the heart, the at least one processor is further configured to direct the system to perform additional operations including:
   determining, based on the motion vector of the first feature point, the third feature point in the target image corresponding to the first feature point;
   determining, based on the motion vector of the second feature point, the fourth feature point in the target image corresponding to the second feature point;
   determining the second distance between the third feature point and the fourth feature point in the target motion phase; and
   determining, based on the first distance and the second distance, a strain value relating to the heart.

6. The system of claim 1, wherein the motion prediction model is trained
   according to an unsupervised learning technique.

7. The system of claim 6, wherein the preliminary model is a generative adversarial network (GAN) model.

8. The system of claim 1, wherein the motion prediction model is generated by minimizing the loss function.

9. The system of claim 1, wherein the predicted second sample image is generated by warping the first sample image of the training sample according to the first motion field.

10. The system of claim 1, wherein the at least one of the one or more iterations further includes:

for each of the at least one training sample,
  generating a second motion field from the second sample image to the first sample image using the preliminary model;
  determining an opposite motion field of the second motion field; and
  determining a second difference between the opposite motion field and the first motion field of the training sample,
  wherein the value of the loss function is determined further based on the second difference corresponding to each training sample.

11. The system of claim 10, wherein the at least one of the one or more iterations further includes:
for each of the at least one training sample,
  generating a predicted first sample image by warping the second sample image of the training sample according to the first sample image of the training sample using the preliminary model;
  generating a third sample image by warping the predicted first sample image according to the second sample image using the preliminary model;
  generating a fourth sample image by warping the predicted second sample image according to the first sample image using the preliminary model; and
  determining a third difference between the third sample image and the second sample image and a fourth difference between the fourth sample image and the first sample image,
  wherein the value of the loss function is determined further based on the third difference and the fourth difference corresponding to each training sample.

12. A non-transitory computer readable medium, comprising a set of instructions for physiological motion measurement, wherein when executed by at least one processor, the set of instructions direct the at least one processor to effectuate a method, the method comprising:
  acquiring a reference image of a region of interest (ROI) corresponding to a reference motion phase of the ROI and a target image of the ROI corresponding to a target motion phase of the ROI, the target motion phase being different from the reference motion phase;
  identifying one or more feature points relating to the ROI from the reference image;
  determining, based on the reference image, a first distance between a first feature point and a second feature point of the one or more feature points, the first feature point and the second feature point being in the reference image corresponding to the in the reference motion phase;
  determining a motion field of the first feature point and the second feature point from the reference motion phase to the target motion phase using a motion prediction model, wherein an input of the motion prediction model includes at least the reference image and the target image;
  determining, based on the motion field, a second distance between a third feature point in the target image, corresponding to the first feature point, and a fourth feature point in the target image, corresponding to the second feature point; and
  determining, based on the first distance and the second distance, a physiological condition of the ROI, wherein the motion prediction model is generated by performing an iteration operation for training a preliminary model using at least one training sample, each of the at least one training sample including a first sample image and a second sample image indicative of a physiological motion of a sample region of interest (ROI), the first sample image corresponding to a first motion phase of the sample ROI, and the second sample image corresponding to a second motion phase of the sample ROI, the iteration operating including one or more iterations, at least one of the one or more iterations including:
for each of the at least one training sample,
  generating a first motion field from the first sample image to the second sample image using an updated preliminary model determined in a previous iteration;
  generating a predicted second sample image according to the first motion field; and
  determining a first difference between the predicted second sample image and the second sample image of the training sample;
  determining, based at least in part on the first difference corresponding to each of the at least one training sample, a value of a loss function; and
  updating the updated preliminary model to be used in a next iteration based on the value of the loss function.

13. A method implemented on a computing device having at least one processor, and at least one storage device, the method comprising:
  acquiring a reference image of a region of interest (ROI) corresponding to a reference motion phase of the ROI and a target image of the ROI corresponding to a target motion phase of the ROI, the target motion phase being different from the reference motion phase;
  identifying one or more feature points relating to the ROI from the reference image;
  determining, based on the reference image, a first distance between a first feature point and a second feature point of the one or more feature points, the first feature point and the second feature point being in the reference image corresponding to the reference motion phase;
  determining a motion field of the first feature point and the second feature point from the reference motion phase to the target motion phase using a motion prediction model, wherein an input of the motion prediction model includes at least the reference image and the target image;
  determining, based on the motion field, a second distance between a third feature point in the target image, corresponding to the first feature point, and a fourth feature point in the target image, corresponding to the second feature point; and
  determining, based on the first distance and the second distance, a physiological condition of the ROI, wherein the motion prediction model is generated by performing an iteration operation for training a preliminary model using at least one training sample, each of the at least one training sample including a first sample image and a second sample image indicative of a physiological motion of a sample region of interest (ROI), the first sample image corresponding to a first motion phase of the sample ROI, and the second sample image corresponding to a second motion phase of the sample ROI, the iteration operating including one or more iterations, at least one of the one or more iterations including:
for each of the at least one training sample,
  generating a first motion field from the first sample image to the second sample image using an updated preliminary model determined in a previous iteration;

generating a predicted second sample image according to the first motion field; and determining a first difference between the predicted second sample image and the second sample image of the training sample;

determining, based at least in part on the first difference corresponding to each of the at least one training sample, a value of a loss function; and updating the updated preliminary model to be used in a next iteration based on the value of the loss function.

14. The method of claim 13, wherein the ROI includes at least one of a heart, a lung, an abdomen, a chest, a stomach of a subject.

15. The method of claim 13, wherein the ROI is a heart, the first feature point relating to the heart in the reference image includes an inner point on an endocardium of the heart, and the second feature point relating to the heart in the reference image includes a corresponding outer point on an epicardium of the heart.

16. The method of claim 15, wherein the identifying the inner point and the corresponding outer point from the reference image includes:

segmenting, from the reference image, the endocardium and the epicardium; and identifying, based on positions of the endocardium and the epicardium, the inner point and the corresponding outer point from the reference image.

17. The method of claim 13, the ROI comprising a heart, wherein the motion field includes a motion vector of the first feature point and a motion vector of the second feature point, and the determining a physiological condition of the heart includes:

determining, based on the motion vector of the first feature point, the third feature point in the target image corresponding to the first feature point;

determining, based on the motion vector of the second feature point, the fourth feature point in the target image corresponding to the second feature point;

determining the second distance between the third feature point and the fourth feature point in the target motion phase; and determining, based on the first distance and the second distance, a strain value relating to the heart.

18. The method of claim 13, wherein the motion prediction model is trained according to an unsupervised learning technique.

19. The method of claim 18, wherein the preliminary model is a generative adversarial network (GAN) model.

20. The method of claim 13, wherein the predicted second sample image is generated by warping the first sample image of the training sample according to the first motion field.

* * * * *